US012736530B2

(12) United States Patent
Gori et al.

(10) Patent No.: US 12,736,530 B2
(45) Date of Patent: Sep. 15, 2026

(54) CONJUGATED COMPOSED OF MEMBRANE-TARGETING PEPTIDES FOR EXTRACELLULAR VESICLES ISOLATION, ANALYSIS AND THEIR INTEGRATION THEREOF

(71) Applicant: TIDES BIO S.R.L., Nus (IT)

(72) Inventors: Alessandro Gori, Arcore (IT); Marina Cretich, Milan (IT); Marcella Chiari, Milan (IT)

(73) Assignee: TIDES BIO S.R.L., Nus (IT)

( * ) Notice: Subject to any disclaimer, the term of this patent is extended or adjusted under 35 U.S.C. 154(b) by 1179 days.

(21) Appl. No.: 17/640,648

(22) PCT Filed: Sep. 4, 2020

(86) PCT No.: PCT/IB2020/058284

§ 371 (c)(1),
(2) Date: Mar. 4, 2022

(87) PCT Pub. No.: WO2021/044381

PCT Pub. Date: Mar. 11, 2021

(65) Prior Publication Data

US 2023/0221307 A1 Jul. 13, 2023

Related U.S. Application Data

(60) Provisional application No. 62/897,042, filed on Sep. 6, 2019.

(51) Int. Cl.

*G01N 21/552* (2014.01)
*G01N 33/543* (2006.01)
*G01N 21/64* (2006.01)
*G01N 21/76* (2006.01)

(52) U.S. Cl.

CPC ....... *G01N 33/5432* (2013.01); *G01N 21/554* (2013.01); *G01N 21/64* (2013.01); *G01N 21/76* (2013.01)

(58) Field of Classification Search

CPC .. G01N 33/5432; G01N 21/554; G01N 21/64; G01N 21/76

See application file for complete search history.

(56) References Cited

FOREIGN PATENT DOCUMENTS

EP 2491952 A1 8/2012

OTHER PUBLICATIONS

Flynn and Yin, J Cellular Physiology, 231: 2327-2332, (Year: 2016).*

Saludes et al., Mol. BioSyst, 9: 2005-2009, (Year: 2013).*

Gori A. et al., "Membrane-binding peptides for extracellular vesicles on-chip analysis manuscript", ChemRxiv, Oct. 25, 2019.

Gori A. et al., "Membrane-binding peptides for extracellular vesicles on-chip analysis", Journal of Extracellular Vesicles, vol. 9, No. 1, Apr. 17, 2020, p. 1751428.

Kulagina N.V. et al., "Antimicrobial peptides for detection of bacteria in biosensor assays", Anal. Chem. 2005, 77, 6504-6508.

Saludes J. P. et al., "Detection of highly curved membrane surfaces using a cyclic peptide derived from synaptotagmin-I", ACS Chemical Biology, vol. 7, No. 10, Jul. 17, 2012, pp. 1629-1635.

Saludes J. P. et al., "Multivalency amplifies the selection and affinity of bradykinin-derived peptides for lipid nanovesicles", Molecular Biosystems, vol. 9, No. 8, Jan. 1, 2013, p. 2005.

Search Report and Written Opinion of PCT/IB2020/058284 of Feb. 2, 2021.

* cited by examiner

*Primary Examiner* — Stacey N Macfarlane

(74) *Attorney, Agent, or Firm* — Silvia Salvadori, P.C.; Silvia Salvadori

(57) ABSTRACT

A molecular probe comprising at least one first moiety and at least one second moiety which are each covalently bound to the molecular probe, wherein: the at least one first moiety comprises at least one binding peptide or peptidomimetic for binding the molecular probe to at least one extracellular vesicle (EV) membrane, wherein the binding is mediated by EV membrane curvature sensing; and the at least one second moiety comprises at least one support binding group for binding of the molecular probe to at least one support. The molecular probe can also comprise a spacer moiety, and/or a labeling moiety, and/or a modification moiety. The molecular probe can be bound to a solid or semi-solid support including a microarray support. The molecular probe can be used in methods in which it is contacted with sample which might include the extracellular vesicle and can involve detection and isolation steps. Kits can include the molecular probe.

14 Claims, 14 Drawing Sheets

Specification includes a Sequence Listing.

| Peptide Code | Sequence | SEQ ID NO |
|---|---|---|
| BP | RPPGFSPFR-K-G-(O2Oc)2-Prg | 1 |
| BPb | $(RPPGFSPFR)_2$-K-G-(O2Oc)2-Prg | 2 |
| BPt | RPPGFSPFR-($O_2$Oc )-RPPGFSPFR-K-G-(O2Oc)2-Prg | 3 |
| BPn | EPPGFSPFE-E-G-(O2Oc)2-Prg | 4 |
| BPs | GRPPRPSFF-K-G-(O2Oc)2-Prg | 5 |
| BPm | RPAGFSAFR-K-G-(O2Oc)2-Prg | 6 |

CONJUGATED COMPOSED OF MEMBRANE-TARGETING PEPTIDES FOR EXTRACELLULAR VESICLES ISOLATION, ANALYSIS AND THEIR INTEGRATION THEREOF

This application is a U.S. national stage of PCT/IB2020/058284 filed on 4 Sep. 2020, which claims priority to and the benefit of U.S. Provisional Application No. 62/897,042 filed on 6 Sep. 2019, the contents of which are incorporated herein by reference in their entireties.

RELATED APPLICATION

The present application claims the benefit of priority of U.S. Provisional Patent Application Ser. No. 62/897,042 filed on Sep. 6, 2019, the entire content of which is incorporated herein by reference.

Sequence listing ASCII file P022877WO-01_Seq Listing.txt, created on Sep. 21, 2022 and of size of 1930 bytes is incorporated herein by reference.

BACKGROUND

Extracellular vesicles (EVs) are membranous micro- and nano-sized biological particles released by cells that play a major role in inter-cellular communication. These membrane-enclosed particles of about 30 to about 1,000 nm in diameter are thought to play important (patho) physiological roles in biological processes, for example, transfer of protein and genetic information, release of cytokines, and degradation of extracellular matrix, angiogenesis, and cell-to-cell communication during cancer progression. These particles are detected in human blood at concentrations of about 5 to about 50 ng/mL and are also found in other biological fluids such as urine, saliva, and cerebrospinal fluid. EVs shuttle an impressive amount of molecular information, including proteins and non-coding RNAs, thus representing a phenomenal source of circulating biomarkers [1]. As such, EVs are arising unparalleled expectations in the field of liquid biopsy and as the next generation theranostic tools [2].

However, to fully realize EVs potential, several challenges in their separation and analysis are yet to be overcome [3]. Indeed, some EVs physicochemical features (e.g. size, buoyant density) overlap those of other nanoscale components of biological fluids, such as high-density lipoproteins (HDLs), viruses, organelles and protein aggregates. These nano-sized “contaminants” can be accidentally co-isolated with EVs through the most common EVs isolation techniques (see general points about isolation methods in Table 1), affecting the downstream analysis of vesicles with regards to their count, function and content [4].

TABLE 1

Common isolation methods for extracellular vesicles

| ISOLATION METHOD | WORKING PRINCIPLE | ADVANTAGES | DRAWBACKS |
| --- | --- | --- | --- |
| Ultra-centrifugation and differential centrifugation | Density | Current gold standard; established protocol; absence of additional chemicals | >4 h; large sample volume; low recovery and purity; costly equipment; complex procedure; possible vesicle rupture; co-isolation of ribosomes and cell debris |
| Density-gradient centrifugation | Density | Current gold standard; high purity; absence of additional chemicals | >4 h; large sample volume; low recovery; costly equipment; complex procedure |
| Co-precipitation (eg Protamine; Sodium Acetate) | Surface charge | Easy and user-friendly | Lack specificity; low scalability; aggregation; contamination with non-EV proteins and/or lipoproteins |
| Size-exclusion chromatography (SEC) | Size and molecular weight | High yield; reproducibility; preserve integrity | Co-isolation of protein aggregates and lipoproteins; one sample at time |
| (Ultra) Filtration | Size difference, separated by filter membranes | Concentration | Damage, deformation; loss of vesicles; filter plugging |
| (Immuno)affinity interaction (eg Tetraspanin antibodies or phospha-tidylserine binding proteins) | Capturing on functionalized magnetic particles | Isolation directly from samples; high selectivity | Low scalability; difficulties in detachment of EVs from particles |
| Polymer-based precipitation (eg PEG) | Precipitation solution form “polymer nets” recovered by low speed centrifugation | Easy and scalable; fast (30 min) | Co-isolation of contaminants like protein aggregates; retention of polymer; poor reproducibility; cost (especially for diluted samples) |

Analytical platforms for EVs high-throughput analysis that do not rely on sample pre-treatment, limiting purification artifacts, are therefore highly desirable. In this scenario, EV microarrays have been introduced by Jørgensen and collaborators to phenotype EVs on a protein microarray platform [5]. In this technique, antibodies are used for the selective capturing of EVs by surface-associated proteins, followed by EVs profiling via fluorescence-based detection of characteristic trans-membrane proteins (CD9, CD63 and CD81). Of note, this approach does not require prior EVs isolation but can be rather directly performed on complex biological samples. This format has been extended to the analysis of antibody captured vesicles in a label free mode using Surface Plasmon Resonance Imaging (SPRi)[6] and Single Particle Interferometric Reflectance Imaging Sensor (SP-IRIS) [7]. Commonly used markers for EV capturing include tetraspanins (CD9, CD63, CD81, CD82), MHC class I and II, HSP70, Annexin V, Flotillin and EpCAM.

However, targeting surface-exposed proteins still present several drawbacks: i) the analysis can be biased by the presence of soluble antigens and EV protein corona; ii) the inherent variability of antibody specificity and affinity can impair EVs capturing efficiency; iii) protein markers relative abundance is subject to significant fluctuations (inter-individual, health status, organ/tissue of origin etc.) that may reduce the value of comparative studies.

The possibility to target a “universal” EVs marker would therefore represent a paradigmatic shift and a first step towards an increased analytical consistence. In this regard, EVs membrane is characterized by physical and chemical traits that are quite peculiar in the extracellular space [8]. Small EVs with diameters of 30-150 nm have indeed highly curved membranes, whose outer leaflets typically contain a high amount of anionic, unsaturated phospholipids together with the presence of characteristic lipid packing defects [9], [10], [11]. For instance, it has been reported that EVs contain 7-8% increase in phosphatidylserine on the outer leaflet of the membrane, whereas, normal cells contain a negligible 0.5-1% amount of phosphatidylserine.

Of note, many proteins are physiologically involved in the dynamic modulation of membrane curvature that occurs during a multitude of cellular processes (including vesicles secretion); it is however particularly remarkable that some of them are able to sense and bind with exquisite selectivity only highly curved membranes [12-15]. These include the Bin-Amphiphysin-Rvs (BAR) [16] domain of ampiphysin, the ArfGAP1 Lipid Packing Sensor (ALPS) proteins [17], the C2B domain of Synaptotagmin-I and the effector domain of the myristoylated alanine-rich C-kinase substrate protein (MARCKS-ED) [18]. Accordingly, membrane sensing peptides have emerged as convenient, easy-to-synthetize novel molecular probes for detecting highly curved membranes [11, 19].

Mechanisms of curvature sensing can be multiple and cooperative. In some cases, the early events of membrane recognition and binding are based on complementary electrostatic interactions between the peptide/protein effector domain and the phospholipids on the outer membrane leaflet, that subsequently can lead to the insertion of the sensing effector into the membrane defects that characterize highly curved membranes. This mechanism is characteristic, but not limited to, of amphipathic helices. Other recognition pathways are characterized by a structural complementarity where curved protein scaffolds match the curvature of membranes. Oppositely, membrane curvature sensing of disordered amino acid chains can be driven by a predominant entropic mechanism. Some groups have proposed membrane targeting peptides as a tool for fluorescence imaging of extracellular vesicles in solution [19-22].

However, to the best of our knowledge, no previous report or claim has been made concerning the possibility to build conjugates based on membrane sensing peptides as described and/or claimed herein that could be favorably exploited for EVs isolation, enrichment or capturing for analytical scopes. In particular, no report apparently deals with supported conjugates such as analytical biochips, microbeads, hydrogel materials, and polymers. In these fields of application, there are many advantages of using peptides and peptide-related probes as they are stable, readily modifiable to tune desired properties, they are inexpensive to prepare even in large scale and don't suffer from batch to batch variability such in the case of antibody preparations. See, for example, WO 2019/039,179.

SUMMARY

Aspects and/or embodiments described and/or claimed herein include, for example, molecular probes, peptides, and/or compositions; methods of making molecular probes, peptides, and/or compositions; methods of using molecular probes, peptides, and/or compositions; and devices and/or kits comprising the molecular probes, peptides, and/or compositions.

For example, a first aspect provides for a molecular probe comprising at least one first moiety and at least one second moiety which are each covalently bound to the molecular probe, wherein: the at least one first moiety comprises at least one binding peptide or peptidomimetic for binding the molecular probe to at least one extracellular vesicle (EV) membrane, wherein the binding is mediated by EV membrane curvature sensing; and the at least one second moiety comprises at least one support binding group for binding of the molecular probe to at least one support.

Another aspect provides for a molecular probe comprising at least one first moiety and at least one second moiety which are each covalently bound to the molecular probe, wherein: the at least one first moiety consists essentially of at least one binding peptide or peptidomimetic for binding the molecular probe to at least one extracellular vesicle (EV) membrane, wherein the binding is mediated by EV membrane curvature sensing; and the at least one second moiety consists essentially of at least one support binding group for binding of the molecular probe to at least one support.

Another aspect provides for a molecular probe comprising at least one first moiety and at least one second moiety which are each covalently bound to the molecular probe, wherein: the at least one first moiety consists of at least one binding peptide or peptidomimetic for binding the molecular probe to at least one extracellular vesicle (EV) membrane, wherein the binding is mediated by EV membrane curvature sensing; and the at least one second moiety consists of at least one support binding group for binding of the molecular probe to at least one support.

In one embodiment, the peptide or peptidomimetic is bound to the at least one extracellular vesicle membrane. In another embodiment, the peptide or peptidomimetic is not bound to the at least one extracellular vesicle membrane.

In one embodiment, the support binding group is bound to the at least one support. In another embodiment, the support binding group is not bound to the at least one support.

In one embodiment, the peptide or peptidomimetic is bound to the at least one extracellular vesicle membrane, and the support binding group is bound to the at least one support. In another embodiment, the peptide or peptidomimetic is not bound to the at least one extracellular vesicle membrane, and the support binding group is not bound to the at least one support.

In one embodiment, the first moiety comprises the peptide. In another embodiment, the first moiety comprises the peptidomimetic.

In one embodiment, the extracellular vesicle is an exosome. In another embodiment, the extracellular vesicle is a microvesicle. In another embodiment, the extracellular vesicle is a synthetic lipidic nanovesicle or microvesicle.

In one embodiment, the binding is not mediated by an EV membrane protein. In one embodiment, the peptide or peptidomimetic is derived from a membrane curvature sensing peptide or protein domain.

In one embodiment, the peptide or peptidomimetic is derived from Bradikinin, MARCKS, Synaptotagmin, Magainin, artgap1, α-synuclein, Synapsin (I), Endophilin, c-reactive protein, or Amphiphysin. In one embodiment, the peptide or peptidomimetic is derived from Bradikinin.

In one embodiment, the first moiety comprises the peptide, and the peptide is a cationic peptide. In one embodiment, the peptide or peptidomimetic is linear, branched, cyclic, tandem, multimeric, multidomain, or multivalent. In one embodiment, the peptide or peptidomimetic is dimeric.

In one embodiment, the support binding group comprises azide, alkyne, thiol, alkene, amine, carboxylic acid, aldehyde, or maleimide. In one embodiment, the support binding group comprises propargyl.

In one embodiment, the probe further comprises at least one third moiety which is covalently bound to the molecular probe and which is a spacer between the first moiety and the second moiety. In one embodiment, the spacer is a single amino acid, an amino acid sequence, an organic moiety, or a cleavable spacer. In one embodiment, the spacer comprises poly(ethylene glycol), lysine, or glycine. In another embodiment, the molecular probe does not further comprise at least one third moiety which is a spacer between the first moiety and the second moiety.

In one embodiment, the probe further comprises at least one fourth moiety which is a label. In one embodiment, the label is a fluorescent label. In another embodiment, the probe does not further comprise at least one fourth moiety which is a label.

In one embodiment, the probe further comprises at least one fifth moiety which is a modifying moiety for the extracellular vesicle and which is a small molecule, a peptide, a protein, a DNA or RNA sequence. In other embodiment, the probe does not further comprise at least one fifth moiety which is a modifying moiety for the extracellular vesicle and which is a small molecule, a peptide, a protein, a DNA or RNA sequence.

Another aspect comprises at least one support comprising at least one molecular probe described and/or claimed herein and bonded to the support, wherein the support is a solid support or a semi-solid support. In one embodiment, the support is a solid support. In another embodiment, the support is a semi-solid support. In one embodiment, the support comprises a chip, a slide, a bead, a well, a hydrogel, a resin, a polymer, a filter, or a membrane. In one embodiment, the support is part of a microarray. In one embodiment, the support comprises a hydrogel. In one embodiment, the support comprises a peptide hydrogel. In one embodiment, the support comprises a partially or completely coated surface adapted for binding to the probe. In one embodiment, the support comprises a partially or completely coated surface adapted for binding to the probe, wherein the coating comprises a polymer. In one embodiment, the support comprises spots or lines for binding to the probe.

Another aspect comprises a method of analysis and/or separation of at least one extracellular vesicle in a sample comprising: providing a support as described and/or claimed herein, and contacting the support with a sample which potentially comprises the extracellular vesicle.

In one embodiment, the method further comprises assaying for the formation of a complex by binding between the extracellular vesicle and the peptide or peptidomimetic of the support. In one embodiment, the assaying method comprises an array method, a microarray method, an ELISA method, a flow cytometry method, a lateral-flow method, a flow-through method, and a bead-based method.

In one embodiment, the assaying method comprises a label-based method. In one embodiment, the label-based method comprises fluorescence, chemiluminescence, or colorimetry.

In another embodiment, the assaying method comprises a label-free method. In one embodiment, the label-free method comprises an interferometric method.

In one embodiment, the assaying method comprises surface plasmon resonance (SPR), single particle-interferometric reflectance imaging sensor (SP-IRIS), or interferometric reflectance imaging sensor (IRIS).

In one embodiment, the assaying method comprises at least two assaying methods. In one embodiment, the assaying method comprises at least one label-free method and at least one label-based method.

In one embodiment, a complex is formed by binding the peptide with the extracellular vesicle from the sample and the bound extracellular vesicle is separated from the sample.

In one embodiment, a complex is formed by binding the peptide with the extracellular vesicle from the sample and the bound extracellular vesicle is isolated from the sample.

In one embodiment, a complex is formed by binding the peptide with the extracellular vesicle from the sample and the bound extracellular vesicle is separated from the peptide or peptidomimetic.

In one embodiment, a complex is formed by binding the peptide with the extracellular vesicle from the sample and the bound extracellular vesicle is separated from the peptide or peptidomimetic with separation occurring at a cleavable spacer of the molecular probe.

In one embodiment, the method is part of an integrated method comprising assaying and isolation of extracellular vesicles.

In one embodiment, the method further comprises modifying the extracellular vesicle.

In one embodiment, the method further comprises modifying the extracellular vesicle while the extracellular vesicle is bound to the peptide or peptidomimetic. In one embodiment, the method further comprises modifying the extracellular vesicle and isolating the modified extracellular vesicle.

Additional aspects include a kit for capturing at least one extracellular vesicle. For example, a kit can comprise at least one molecular probe as described and/or claimed herein. In addition, the kit can comprise at least one support as described and/or claimed herein. The kit can be adapted to assist carrying out any one of the methods described and/or claimed herein.

In preferred embodiments, aspects and/or embodiments of the presently described and/or claimed inventions relate to peptide-based molecular conjugates that can be used, for example, for extracellular vesicles assays, detection, and isolation from various samples and also, for example, for the integrated extracellular vesicles isolation and analysis. More particularly, preferred aspects and/or embodiments of the present inventions relate to, for example, extracellular vesicles membrane binding peptides which are in suitable form for the stable immobilization onto diverse solid supports to be used for analysis and isolation, and for the incorporation within, for example, hydrogels and polymers. In preferred embodiments, peptidic probes can be bound to the different supports with controllable orientation and tuneable multivalency.

More particular embodiments described herein include compositions, methods and uses for the development of, for example, conjugates of peptides/peptidomimetics and peptide-based molecules and their salts capable of detecting and binding to extracellular vesicles (EVs) through phospholipid/curvature membrane recognition (e.g., can be called EV sensors) with different spacing and functional moieties to be exploited for conjugation purposes on different supports. Together, the resulting conjugates can be referred to as "peptidic probes".

In particular, embodiments disclosed herein concern the compositions and uses for, for example, peptides and derivatives thereof that are derived from membrane binding peptides and protein domains such as, for example, Bradykinin (BRK), MARCKS, Annexin V, OmpA and other peptides and derivatives thereof. In particular embodiments, compositions can include either linear peptide sequences and multivalent presentation forms (branched ramifications, tandem repeats), and can include different spacers and functional chemical handles to be exploited for conjugation purposes. In additional particular embodiment, peptidic probes can be cyclic or linear depending on affinity to associate with EVs contained in biological samples or their derivatives, and their multivalent presentation can be also the result of spatial proximity exposure of linear chemical entities upon surface binding.

Compositions and methods can also include a set of different chemical strategies for the selective and oriented binding of the peptidic probes onto, for example, analytical surfaces, solid supports, microbeads, polymers and hydrogel materials. Compositions and methods can also include, for example, a set of different chemical strategies and cleavable and stimuli responsive linkers for release of captured EVs In accordance with these embodiments, particular compositions comprising, for example, the described peptidic probes can be used to detect and bind EVs with, for example, curved, negatively charged membranes for purposes of on-chip capturing and analysis with various label-based and label-free detection schemes, isolation from biological samples (followed by possible release of captured vesicles) by microbeads, flow-through columns, filters, hydrogels, and polymers for vesicles pull-down by centrifugation, and use in platforms for integrated isolation and diagnostic purposes.

Also described are, for example, strategies for the oriented probes conjugation to different solid supports which greatly enhance peptidic probes binding efficiency of EVs and that multivalent presentation enhance EV capturing.

Applications include, for example, on-chip EVs analysis (microarray format with different detection schemes including fluorescence, interferometry, surface plasmon resonance), EVs isolation from various sources including complex biological samples (e.g. serum, plasma, urine), and the conjugation on platforms for integrated isolation and analysis.

Additional advantages include, for example, enhanced EV capturing capacity compared to antibodies or ligands directed against individual EV surface protein markers, as well as general and unbiased EV detection for quantification and reference purposes.

DETAILED DESCRIPTION

Introduction and Definitions

Figures 1, 2:
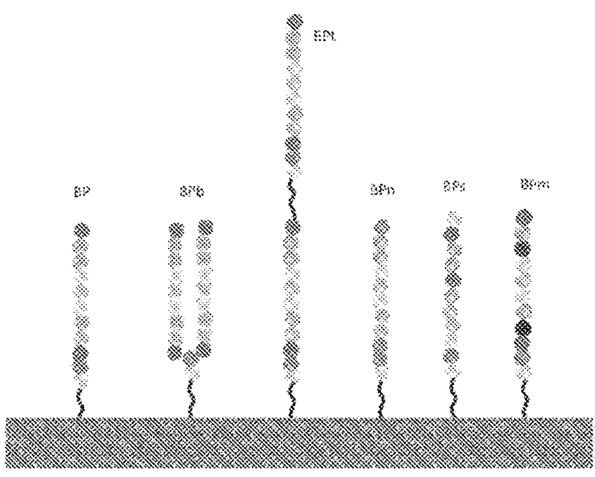
FIG. 1: sequences of the tested peptides modified with short-chain PEG spacers $(CH_2CH_2O)_x$ bearing a terminal propargylglycine (Prg).
FIG. 2: scheme of mono and multi-valent presentations of the different peptides immobilized on analytical chip.

All references cited herein are incorporated by reference in their entirety.

In the following sections, various exemplary compositions and methods are described in order to detail various embodiments of the claimed inventions. Practicing the various embodiments does not require the employment of all or even some of the details outlined herein, but rather, peptidic sequences chosen, spacers, reactive chemical handles and functional groups, proteins and antibodies selected, samples, concentrations, times and other details may be modified through routine experimentation. In some cases, well-known and routinely used methods or components have not been included in the description. For example, there may be employed conventional organic chemistry, peptide chemistry, protein chemistry, polymer chemistry, and molecular biology within the skill of the art. References to the literature for some techniques are present in the text.

The open terms "comprising" or "comprises" also include within their purview as sub-embodiments (more narrow embodiments) the semi-closed terms "consisting essentially of" or "consists essentially of," as well as the closed terms "consisting of" and "consists of."

As disclosed herein, an "EVs source" can mean a biological, synthetic or commercial source of, for example, 10-1,000 nm sized lipid vesicles, or 10-200 nm sized lipid nanovesicles. This term includes but it is not limited to cell culture supernatant, a non-processed biofluid, a biofluid, and/or a commercial EV preparation As disclosed herein, "isolation" can mean the process by which EVs are obtained (enriched and/or recovered) starting from an EV source. EV isolation can occur on a solid support (chip surface, microbead, filter) or through a semi-solid support (hydrogel, polymer, resin) or flowing through a membrane or a filter.

As disclosed herein, "analysis" or "detection" can mean any chemical, biological or physical analytical process intended to reveal a chemical, biological or physical feature or property of EVs that can be exploited to extrapolate information of EVs presence, number, size, composition, cargo, mechanical property.

As disclosed herein, support binding group can be part of the structure of a molecule characterized by specific elements and a well-defined and precise structure, which gives the compound a typical reactivity similar to that of other compounds containing the same group and which in this context is introduced to give the peptide a specific reactivity (orthogonal) with a counterpart present on the immobilization support As disclosed herein, spacer can be chemically and functionally inert molecule introduced in the relative context for the sole purpose of distancing the active molecule from the surface in space.

As disclosed herein, functional polymer can be polymer used to coat the supports and favor the immobilization of the peptides by (functional) groups reactive with a counterpart present in the peptide.

As disclosed herein, a non-covalent interaction can be any molecular interaction that is not strictly based on a covalent bond as known in the art. As such, non-covalent interactions can be, for instance, electrostatic interactions, pi interactions, van der Waals interactions, hydrophobic effects, and hydrogen bonding.

A first aspect, which is hereinafter described in more detail, provides for a molecular probe comprising at least one first moiety and at least one second moiety which are each covalently bound to the molecular probe, wherein: the at least one first moiety comprises at least one binding peptide or peptidomimetic for binding the molecular probe to at least one extracellular vesicle (EV) membrane, wherein the binding is mediated by EV membrane curvature sensing; and the at least one second moiety comprises at least one support binding group for binding of the molecular probe to at least one support.

The peptide or peptidomimetic can be derived from the naturally occurring aminoacidic sequence of a peptide or protein domain with membrane binding properties.

The first and second moieties can be covalently linked to each other, directly or indirectly.

The molecular probe can exist in different forms or embodiments. For example, the molecular probe can be in a form for binding or covalent reaction to occur, or it can be in a form after that binding or covalent reaction has occurred.

For example, in one embodiment, the peptide or peptidomimetic of the molecular probe is not bound to the at least one extracellular vesicle membrane, whereas in another embodiment, the peptide or peptidomimetic is bound to at least one extracellular vesicle membrane.

In one embodiment, the support binding group of the molecular probe is not bound to the at least one support, whereas in another embodiment, the support binding group is bound to the at least one support.

In another embodiment, the peptide or peptidomimetic of the molecular probe is not bound to the at least one extracellular vesicle membrane, and the support binding group of the molecular probe is also not bound to the at least one support.

In another embodiment, the peptide or peptidomimetic of the molecular probe is bound to the at least one extracellular vesicle membrane, and the support binding group of the molecular probe is also bound to the at least one support.

In another embodiment, the peptide or peptidomimetic of the molecular probe is not bound to the at least one extracellular vesicle membrane, but the support binding group of the molecular probe is bound to the at least one support. In contrast, in another embodiment, the peptide or peptidomimetic of the molecular probe is bound to the at least one extracellular vesicle membrane, but the support binding group of the molecular probe is not bound to the at least one support.

Peptide sequences are known in the art and, as disclosed herein, peptide sequences are reported according to the conventional one letter code or to the conventional three letter code.

Where moieties are specified by their conventional chemical formulae, written from left to right, they equally encompass the chemically identical moieties that would result from writing the structure from right to left, e.g., —$CH_2O$— is equivalent to —$OCH_2$—.

Peptidic probes can include peptides (average size of about 5 to about 30-residues, but not limited to this size), peptide variants and derivatives, peptidomimetics that share the ability to bind to EVs membranes. Peptidic probes can be also contain or can be entirely constituted by either L- or D-amino acids.

Peptide "variants" or "derivatives" are known in the art and can be used. The terms "variant" or "derivative" in relation to the amino acid sequences includes any substitution of, variation of, modification of, replacement of, inversion of (scrambling), deletion of or addition of one (or more) amino acids from or to the sequence providing the resultant amino acid sequence preferably has targeting activity, preferably having at least 25 to 50% of the activity as the peptides presented in the sequence listings, more preferably at least substantially the same activity.

Sequences may be modified for use in the embodiments of the presently claimed inventions. Typically, modifications are made that maintain the activity of the sequence. Thus, in one embodiment, amino acid substitutions may be made, for example, from 1, 2 or 3 to 10 or 20 substitutions provided that the modified sequence retains at least about 25 to 50% of, or substantially the same activity. However, in an alternative embodiment, modifications to the amino acid sequences of a molecular probe may be made intentionally to reduce the binding properties of the probe.

Amino acid substitutions may include the use of non-naturally occurring analogues, for example, to increase chemical stability or stability to bio-samples.

Conservative substitutions may be made, for example, according to the Table below. As known in the art, amino acids in the same block in the second column and, preferably, in the same line in the third column may be substituted for each other:

| | | |
|---|---|---|
| Aliphatic | Non polar | GAP |
| Aliphatic | Non polar | ILV |
| Aliphatic | Polar uncharged | CSTM |
| Aliphatic | Polar uncharged | NQ |
| Aliphatic | Polar charged | DE |
| Aliphatic | Polar charged | KRH |
| Aromatic | — | FWY |

Molecular probes can also include fragments of the peptides and variants thereof, including fragments of the sequences. Preferred fragments include those which include a binding domain.

The molecular probe can comprise both amino acid and non-amino acid moieties. The non-amino acid moieties can be used as part of the support binding group to bind to a support or for labeling.

Strategies for post-synthesis modification of molecular probes can include chemical ligation techniques, enzymatic modifications, or any other known technique for peptide and protein modifications.

The molecular probe may be used in combination with one or a plurality of peptidics or peptidomimetics in the first moiety. The combination may comprise a cocktail (a mixture) of individual peptidic or peptidomimetic probes or it may be in the form of a fusion peptidic or peptidomimetic probe or a multi-domain peptidic or peptidomimetic probe. Two or more copies of a peptidic probe may be joined to one another, alone or in combination with one more additional peptidic or peptidomimetic probes, or joined through a molecular scaffold.

A peptidic probe of the invention may be used in combination with one or more additional peptides or peptidic probes. The combination may comprise a cocktail (a simple mixture) of individual peptidic probes or it may be in the form of a fusion peptidic probe or a multi-domain peptidic probe. Two or more copies of a peptidic probe of the invention may be joined to one another, alone or in combination with one more additional peptidic probes, or joined through a molecular scaffold.

First Moiety for Binding Probe to EV Membrane

The peptide or peptidomimetic of the first moiety is adapted so that the binding is mediated by EV membrane curvature sensing. EV membrane curvature sensing is known in the art but has not been used as described and/or claimed herein. The binding to the EV membrane can be such that the binding is not mediated by a membrane protein of the EV membrane. The peptide or peptidomimetic can be derived from the naturally occurring aminoacidic sequence of a peptide or protein domain with membrane binding properties.

Peptide or peptidomimetics can be used in the first moiety. Peptidomimetics or "peptide mimetics" are known in the art and can be used in place of the peptidic EV-membrane binding moiety in the first moiety. Mimetics are peptide-containing molecules which mimic elements of protein or peptide secondary structure. The underlying rationale behind the use of peptide mimetics is that the peptide backbone of proteins exists chiefly to orient amino acid side chains in such a way as to facilitate molecular interactions. A peptide mimetic permits molecular interactions similar to the original molecule.

In one embodiment, the extracellular vesicle is an exosome or a microvesicle. In one embodiment, the extracellular vesicle is an exosome, and in another embodiment, the extracellular vesicle is a microvesicle.

The first moiety of the molecular probe can be generated based on its ability to associate with extracellular vesicles by, for example, binding to smaller diameter vesicles (e.g., 10 nm to 150 nm diameter, or 30 nm to 100 nm scale) by detecting curvature of the vesicle versus that of a larger vesicle of a few to several hundred nanometer as known in the art.

In one embodiment, the peptide or peptidomimetic is derived from Bradikinin, MARCKS, Synaptotagmin, or Amphiphysin. In one embodiment, the peptide or peptidomimetic is derived from Bradikinin; in another embodiment, it is derived from MARCKS; in another embodiment, it is derived from Synaptotagmin; and in another embodiment, it is derived from Amphiphysin.

In one embodiment, the peptide or peptidomimetic is cyclic, multimeric, multidomain, or multivalent. In one embodiment, it is cyclic; in another embodiment, it is multimeric; in another embodiment, it is multidomain; and in another embodiment, it is multivalent.

The first moiety comprising the peptide or peptidomimetic is adapted to couple to the molecular probe and in some cases couple directly to the second moiety having the support binding group for binding to a support.

Second Moiety for Binding Probe to Support

The support binding group of the second moiety can be nucleophilic or electrophilic in its capacity to bind to a support. Support binding groups can provide covalent binding or specific binding to the support. Groups such as biotin, avidin, streptavidin, and analogues thereof, can be used. The support binding group can also be represented by a oligopeptide, oligonucleotide or hybrid sequence that provide stable binding to the support through non-covalent interactions.

For example, the support binding group can comprise azide, alkyne, thiol, alkene, amine, carboxylic acid, aldehyde, or maleimide.

In one embodiment, the support binding group can be or can comprise an amino acid, including a non-natural amino acid, such as, for example, propargylglycine. This can react with, for example, an azide group on the support.

Another example is a polyhistidine functional group.

The second moiety is also adapted for bonding to the first moiety.

In some embodiments, the support binding group is linked to the peptidic probe N-terminus or C-terminus, thus minimizing any interference in the binding of the probe to the EV membrane. Alternatively, the support binding group can be linked to amino acid residues which are amido- or carboxylic-bond acceptors, which may be naturally occurring on the molecule or artificially inserted using chemical techniques.

Preferred embodiments include the following, including combinations of these embodiments:

- the first moiety comprises the peptide; or the first moiety comprises the peptidomimetic;
- the extracellular vesicle is an exosome; the extracellular vesicle is a microvesicle; or the extracellular vesicle is a synthetic lipidic nanovesicle or microvesicle;
- the binding is not mediated by an EV membrane protein; or the peptide or peptidomimetic is derived from a membrane curvature sensing peptide or protein domain;
- the peptide or peptidomimetic is derived from Bradikinin, MARCKS, Synaptotagmin, Magainin, arfgap1, α-synuclein, Synapsin (I), Endophilin, c-reactive protein, or Amphiphysin; or the peptide or peptidomimetic is derived from Bradikinin.
- the first moiety comprises the peptide, and the peptide is a cationic peptide; or the peptide or peptidomimetic is linear, branched, cyclic, tandem, multimeric, multidomain, or multivalent; the peptide or peptidomimetic is dimeric.
- the support binding group comprises azide, alkyne, thiol, alkene, amine, carboxylic acid, aldehyde, or maleimide; or the support binding group comprises propargyl.

Third Moiety: Optional Spacer Embodiment

The molecular probe, optionally, can comprise at least one third moiety comprising at least one spacer. Spacers, or linkers, are known in the art.

The peptide or peptidomimetic group (first moiety) can be coupled directly to the peptide binding group (second moiety) used or indirectly through a spacer. The spacer is not particularly limited but can be, for example, a single amino acid (e.g., G (glycine)), an amino acid sequence or an organic residue, such as 3,6-dioxaoctanoic acid, amino hexanoic acid, or others. The spacer can be hydrophilic or hydrophobic, or it can have hybrid properties.

A spacer can be cleavable, meaning it can be broken in one or more parts following a stimulus, leading to the release of the bound EV membrane. Stimuli that can be used to actuate spacer cleavage are diverse, including but not limited to: pH, reducing agents, UV radiation, IR radiation, temperature, metals, ions, chelating agents, detergents, chemicals, and enzymes.

In a preferred embodiment, the probe further comprises at least one third moiety which is covalently bound to the molecular probe and which is a spacer between the first moiety and the second moiety. The spacer can be, for example, a single amino acid, an amino acid sequence, an organic moiety, or a cleavable spacer. The spacer can comprise, for example, poly(ethylene glycol), lysine, or glycine.

In another embodiment, the molecular probe does not further comprise at least one third moiety which is a spacer between the first moiety and the second moiety.

Fourth Moiety: Optional Label Embodiment

The molecular probe, optionally, can comprise at least one fourth moiety for labeling the probe, with site-specific labeling with signal molecules, including, for example, fluorophores, enzymes, or quantum dots. Labeling is known in the art.

The probe further comprises at least one fourth moiety which is a label, including for example a fluorescent label.

In one embodiment, however, the probe does not further comprise at least one fourth moiety which is a label.

Fifth Moiety: Optional Embodiment for Modifying Moiety for the Extracellular Vesicle The molecular probe, optionally, can comprise at least one fifth moiety for modifying (e.g., functionalizing or decorating) the EV. This moiety is distinct from the third and/or fourth moieties. The fifth moiety for modifying can be, for example, at least one small molecule. Examples include without limit drugs or sugars or with other molecules including, for example, DNA/RNA sequences, peptides or proteins.

In particular, the probe can further comprise at least one fifth moiety which is a modifying moiety for the extracellular vesicle and which is a small molecule, a peptide, a protein, a DNA or RNA sequence.

In another embodiment, the probe does not further comprise at least one fifth moiety which is a modifying moiety for the extracellular vesicle and which is a small molecule, a peptide, a protein, a DNA or RNA sequence.

Methods for Making and Purifying Molecular Probes

Methods known in the art can be used to make the molecular probes.

Conjugates include fusion products in which the peptide or targeting moiety is produced through genetic expression of a DNA molecule encoding these constructs, directly synthesised conjugates and coupled conjugates in which pre-formed moieties are associated by a cross-linking agent. The term is also used herein to include associations, such as aggregates.

Some embodiments for generating molecular probes include solid phase peptide synthesis (SPPS). Certain solid phase chemistry techniques include the incorporation on non amino acidic spacers and/or reactive functional groups or chemical handles. Techniques known in the art can be also used to generate cyclic peptides and peptidomimetics. Certain embodiments include generating multivalent chemical entities on a solid substrate. Peptides generated by methods disclosed herein can be evaluated by spectroscopic techniques as well as being tested for binding to EV membranes.

Various techniques suitable for use in peptidic probes, proteins or antibodies purification are known to those of skill in the art. These include, for example, precipitation with diethyl ether followed by centrifugation; chromatography steps such as ion exchange, gel filtration, reverse phase and affinity chromatography; isoelectric focusing; gel electrophoresis; dialysis, and combinations of such and other techniques. As is generally known in the art, it is believed that the order of conducting the various purification steps may be changed, or that certain steps may be omitted, and still result in a suitable method for the preparation of a purified product.

There is no general requirement that a chemical entity is to be always provided in the most purified state. It is contemplated that less substantially purified products will have utility in certain embodiments. Partial purification may be accomplished by using fewer purification steps in combination, or by utilizing different forms of the same general purification scheme. Methods exhibiting a lower degree of relative purification may have advantages in total recovery of product, or in maintaining the activity.

Some embodiments include generating peptides or peptidomimetics using recombinant technologies. Any method known in the art can be used for generating peptides or peptidomimetics disclosed herein. Examples of expression systems known to the skilled practitioner in the art include bacteria such as *E. coli*, yeast such as *Pichia pastoris*, baculovirus, and mammalian expression systems. A complete gene can be expressed or, alternatively, fragments of the gene encoding portions of peptidic probes can be produced. Genes or gene segments that encode peptidic probes or part of them may be inserted into an expression vector by known subcloning techniques and expressed in a vector The engineering of DNA segment(s) for expression in a prokaryotic or eukaryotic system may be performed by techniques generally known to those of skill in recombinant expression. It is believed that virtually any expression system may be employed for these techniques. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Any method known in the art related to site-specific mutagenesis is contemplated of use herein.

Support

The molecular probes are adapted to bind to and used with at least one support or, more particularly, at least one surface of at least one support. The support can also be termed a "carrier," and supports and carriers, along with their surfaces, are known in the art. For example, the support can be solid, or it can be semi-solid. In one embodiment, the support comprises a chip, a slide, a bead, a well, a hydrogel, a resin, a polymer, a filter, or a membrane. The support can be, for example, part of a microarray. The support can comprise a hydrogel including, for example, a peptide hydrogel.

The support can comprise a partially or completely coated surface adapted for binding to the probe. The support can comprise a partially or completely coated surface adapted for binding to the probe, wherein the coating comprises a polymer.

The support can comprise spots or lines for binding to the probe.

Examples include microscale and nanoscale beads, as well as hydrogels including hydrogels made by self-assembling peptide hydrogelators. The binding to the support can be covalent or non-covalent, and can be facilitated and spatially oriented by a moiety associated with the peptide that enables covalent or non-covalent binding, such as a moiety that has a high affinity to a component attached to the carrier, support or surface. As a non-limiting example, the molecular probe can bring a biotin moiety, and the component associated with the surface or other support can be avidin. In another example, click-chemistry can be used to bind the molecular probe to a support coated by a functional polymer. The peptide can be immobilized on the solid or semi-solid surface or carrier either prior to or after the addition of the sample containing EVs.

In embodiments of the invention, the solid or semi-solid surface or carrier is a slide or chip for microarrays, the floor or wall in a microtiter well; a filter surface or membrane (e.g. a nitrocellulose membrane or a PVDF (polyvinylidene fluoride) membrane, such as an Immobilon membrane); a hollow fiber; a peptidic hydrogel or any other synthetic or natural hydrogel, a natural or synthetic polymer; a beaded chromatographic medium (e.g. an agarose or polyacrylamide gel); a magnetic bead; a fibrous cellulose matrix; an HPLC matrix; an FPLC matrix; a substance having molecules of such a size that the molecules with the peptidic probe bound thereto, when dissolved or dispersed in a liquid phase, can be retained by means of a filter; a substance capable of forming micelles or participating in the formation of micelles allowing a liquid phase to be changed or exchanged without entraining the micelles; a water-soluble polymer; or any other suitable carrier, support or surface.

As the carrier pertaining to the present invention, any carrier can be used as long as it is an insoluble carrier, and includes an organic substance, such as, polystyrene, polyacrylic acid, polymethacrylic acid, polymethyl methacrylate, polyacryl amide, polyglycidyl methacrylate, polypropylene, polyolefin, polyimide, polyurethane, polyester, polyvinyl chloride, polyethylene, polychlorocarbonate, a silicone resin, silicone rubber, agarose, dextran, an ethylene-maleic anhydride copolymer, or the like; a natural or synthetic polymer; a natural or synthetic hydrogel including hydrogels made by self-assembling peptide hydrogelator; an inorganic substance, such as glass, silicon oxide, diatomaceous earth, porous glass, obscured glass, alumina, silica gel, a metal oxide, or the like; a magnetic substance, such as iron, cobalt, nickel, magnetite, chromite, or the like; and those prepared using alloys of these magnetic substances as raw materials. In addition, these carriers may be used in a wide variety of forms, such as a plain or nanostructured surface, a microplate, a tube, a microchannel, pillars, a disk-like piece, particles (beads), and the like.

The association of the peptidic probe to the carrier can be either covalent or non-covalent, and the non-covalent immobilization can be non-specific (e.g. non-specific binding to a polystyrene surface in e.g. a microtiter well). Selective or semi-selective binding to a solid or semi-solid carrier, support or surface, can be achieved by the peptidic probe bringing a reactive moiety (chemical handle or functional group) or an additional peptidic, oligonucleotide or hybrid sequence which enables its covalent or non-covalent binding to the solid or semi-solid carrier, support or surface. For example, the moiety can have affinity to a component attached to the carrier, support or surface. In this case, the moiety can be, e.g., a biotin or biotinyl group or an analogue thereof bound to the peptidic probe, and the component is then avidin, streptavidin or an analogue thereof. An alternative is a situation in which the peptidic probe has a poly-Histidine tag and the carrier comprises a Nitrilotriacetic Acid derivative (NTA) charged with $Ni^{++}$ ions. A non-limiting list of other common chemical handles and reactive groups that can be included for conjugation purposes used in the peptidic probes of the present invention is azides, alkynes, thiols, alkenes, amines, carboxylic acids, aldehydes, maleimides. Among suitable carriers, supports or surface are, e.g., magnetic beads or latex of co-polymers such as styrene-divinyl benzene, hydroxylated styrene-divinyl benzene, polystyrene, carboxylated polystyrene, beads of carbon black, non-activated or polystyrene or polyvinyl chloride activated glass, epoxy-activated porous magnetic glass, gelatin or polysaccharide particles or other protein particles, mono- or polyclonal antibodies or Fab fragments of such antibodies.

Different embodiments can be used for bonding the peptide binding group of the molecular probe to a support. Examples include copper-catalyzed azide-alkyne cycloaddition (click chemistry); strain promoted azide-alkyne cycloaddition (copper free click chemistry); thiol-maleimide conjugation; amide bond formation promoted by carboxyl groups activators: and biotin-streptavidin mediated conjugation. Literature references to these protocols can be also found in the literature. See, for example, US Patent Publications 2016/0200847; 2016/0228842; 2015/0087555; and 2013/0115382.

Microarray

Microarrays are known in the art, and the support and other elements of the described embodiments can be integrated into a microarray. The microarrays can be patterned with geometrically defined patters including spots and lines as known in the art.

Samples and Evs to be Analyzed

The sample which potentially comprises an EV is not particularly limited. The sample can be taken, for example, from any biological tissue. The sample can be pre-treated or modified before it is subjected to further use with the molecular probes described herein.

Methods of Using Peptides

The methods described herein can be used in methods such as, for example, assays, isolations, and membrane modification, functionalization, and/or decoration. Tools known in the art such as, for example, buffers, proteins and antibodies selected, samples, concentrations, times and other details may be used and modified.

A method of analysis and/or separation of at least one extracellular vesicle in a sample comprising: providing a support as described and/or claimed herein, and contacting the support with a sample which potentially comprises the extracellular vesicle.

The method can further comprise assaying for the formation of a complex by binding between the extracellular vesicle and the peptide or peptidomimetic of the support. The assaying method can comprise, for example, an array method, a microarray method, an ELISA method, a flow cytometry method, a lateral-flow method, a flow-through method, and a bead-based method. The assaying method can comprise a label-based method, including for example methods comprising fluorescence, chemiluminescence, or colorimetry. The assaying method can comprise a label-free method, including for example an interferometric method. The assaying method can comprise, for example, surface plasmon resonance (SPR), single particle-interferometric reflectance imaging sensor (SP-IRIS), or interferometric reflectance imaging sensor (IRIS).

The assaying method can comprise at least two assaying methods, including where, for example, the assaying method comprises at least one label-free method and at least one label-based method.

In one embodiment, a complex is formed by binding the peptide with the extracellular vesicle from the sample and the bound extracellular vesicle is separated from the sample. In one embodiment, a complex is formed by binding the peptide with the extracellular vesicle from the sample and the bound extracellular vesicle is isolated from the sample. In one embodiment, a complex is formed by binding the peptide with the extracellular vesicle from the sample and the bound extracellular vesicle is separated from the peptide or peptidomimetic. In one embodiment, a complex is formed by binding the peptide with the extracellular vesicle from the sample and the bound extracellular vesicle is separated from the peptide or peptidomimetic with separation occurring at a cleavable spacer of the molecular probe.

In some embodiments, the method is part of an integrated method comprising assaying and isolation of extracellular vesicles.

In some embodiments, the method further comprises modifying the extracellular vesicle (see above description for the fifth moiety). In some embodiments, the method further comprises modifying the extracellular vesicle while the extracellular vesicle is bound to the peptide or peptidomimetic. In some embodiments, the method further comprises modifying the extracellular vesicle and isolating the modified extracellular vesicle.

More particularly, one embodiment of the invention is an EV detection method, which includes (1) taking a biological sample such as a body fluid or tissue likely to contain EVs; (2) contacting the sample with a molecular probe of the invention associated to a substrate, under conditions effective for the formation of a specific peptidic probe-EV complex (for specific binding of the peptidic probe to the EV), e.g., reacting or incubating the sample and a peptidic probe; and (3) assaying the surface for the presence of an EV-probe reaction (e.g., determining the amount of an EV-probe complex).

In embodiments of the invention, the assay may comprise, for example, immobilizing a molecular probe of the invention, adding the sample containing EVs and then detecting the amount of EV bound to the probe, e.g. by adding a labeled substance (conjugate, binding partner), such as a labeled antibody, which specifically recognizes the EVs.

Immobilization of a peptidic probe of the invention can be either covalent or non-covalent, and the non-covalent immobilization can be non-specific (e.g. non-specific binding to a polystyrene surface in e.g. a microtiter well). Selective or semi-selective binding to a solid or semi-solid carrier, support or surface, can be achieved by the peptidic probe bringing a reactive moiety (chemical handle or functional group) which enables its covalent or non-covalent binding to the solid or semi-solid carrier, support or surface. For example, the moiety can have affinity to a component attached to the carrier, support or surface. In this case, the moiety can be, e.g., a biotin or biotinyl group or an analogue thereof bound to the peptidic probe, and the component is then avidin, streptavidin or an analogue thereof. An alternative is a situation in which the peptidic probe has a poly-Histidine tag and the carrier comprises a Nitrilotriacetic Acid derivative (NTA) charged with $Ni^{++}$ ions. A non-limiting list of other common chemical handles and reactive groups that can be included for conjugation purposes used in the peptidic probes of the present invention includes azides, alkynes, thiols, alkenes, amines, carboxylic acids, aldehydes, and maleimides. Among suitable carriers, supports or surface are, e.g., magnetic beads or latex of co-polymers such as styrene-divinyl benzene, hydroxylated styrene-divinyl benzene, polystyrene, carboxylated polystyrene, beads of carbon black, non-activated or polystyrene or polyvinyl chloride activated glass, epoxy-activated porous magnetic glass, gelatin or polysaccharide particles or other protein particles.

Devices for performing specific binding assays, are known and can be readily adapted for use in the present methods. Solid phase assays, in general, are easier to perform than heterogeneous assay methods which require a separation step, such as precipitation, centrifugation, filtration, chromatography, or magnetism, because separation of reagents is faster and simpler. Solid-phase assay devices include microarray slides, microtiter plates, flow-through assay devices, dipsticks and immunocapillary or immunochromatographic or immunoassay devices.

In one embodiment of the invention, peptides of the invention are immobilized onto beads (microspheres), for flow-cytometry based methods for analyzing and/or detecting EVs.

As described above, in some embodiments of the invention, the peptidic probe is provided with a suitable label which enables detection. Conventional labels may be used which are capable, alone or in concert with other compositions or compounds, of providing a detectable signal. Suitable detection methods include, e.g., detection of an agent which is tagged, directly or indirectly, with a fluorescent label by immunofluorescence microscopy, including confocal microscopy, or for flow cytometry (FACscan); detection of a radioactively labeled agent by autoradiography; electron microscopy.

In one embodiment, a radioactive element (e.g. a radioactive amino acid) can be incorporated directly into a peptidic chain; in another embodiment, a fluorescent label is associated with a peptidic probe via biotin/avidin interaction, association with a fluorescein conjugated antibody, or the like. In one embodiment, a detectable specific binding partner for the antibody is added to the mixture. For example, the binding partner can be a detectable by an antibody. This secondary antibody can be labeled, e.g., with a radioactive, enzymatic, fluorescent, luminescent, or other detectable label, such as an avidin/biotin system.

A "detection system" for detecting EV-peptidic probe complex, as used herein, may comprise a detectable binding partner, such as an antibody specific for the peptidic probe. In one embodiment, the binding partner is labeled directly. In another embodiment, the binding partner is attached to a signal generating reagent, such as an enzyme that, in the presence of a suitable substrate, can produce a detectable signal. A surface for immobilizing the peptidic probe may optionally accompany the detection system.

In embodiments of the invention, the detection procedure comprises detection by change of refractive index in the EV-peptidic probe complex that can be detected by interferometry or surface plasmon resonance In embodiments of the invention, the detection procedure comprises visibly inspecting the EV-peptidic probe complex for a color change, or inspecting the EV-peptidic probe complex for a physical-chemical change. Physical-chemical changes may occur with oxidation reactions or other chemical reactions. They may be detected by eye, using a spectrophotometer, or the like.

In one embodiment of the method, the peptidic probe, or a mixture of peptidic probs, is electro- or dot-blotted onto nitrocellulose paper. Subsequently, the biological fluid (e.g. serum, plasma, saliva) is incubated with the blotted antigen, and EV in the biological fluid is allowed to bind to the antigen(s). The bound antibody can then be detected, e.g. by standard immunoenzymatic methods.

In another embodiment of the method, latex or polystyrene beads are conjugated to the peptidic probe of the invention. Subsequently, the biological fluid is incubated with the bead/peptidic probe conjugate, thereby forming a reaction mixture. The reaction mixture is then analyzed to determine the presence of the Evs One assay for the analysis is a microarray based EV analysis (EV arrays). In the EV array, the peptide of the invention is spotted and bound to the surface of a microarray slide or chip directly or through a capture matrix (i.e., functional polymer coating, streptavidin/avidin system). Residual, non-specific protein-binding sites on the surface are then blocked with an appropriate agent, such as ethanolamine, bovine serum albumin (BSA), a buffered solution of nonfat dry milk. The microarray is then incubated with a biological sample potentially, optionally, or likely containing EVs (e.g., cell culture supernatant, serum, plasma, saliva, CSF). The sample can be applied neat, or more often it can be diluted, usually in a buffered solution which contains a small amount (0.1-5.0% by weight) of protein, such as BSA and detergent such as Tween 20. After incubating for a sufficient length of time to allow specific binding to occur, the chip/slide is washed to remove unbound material. The slide can be subjected to label-free detection for example by SP-IRIS (Single Particle Interferometric Reflectance Imaging Sensors) for digital counting of immobilized EVs or other interferometric detection or to Surface Plasmon Resonance and other plasmonic detection.

In one embodiment the microarray is then incubated with an optimal concentration of an appropriate antibody (e.g., for specific EV markers such as CD9, CD63, CD81) or other ligand (e.g., peptide, aptamer) that is conjugated to a fluorescence label or a quantum dot or an enzyme or other label. The label can be chosen from a variety of fluorescent, chemiluminescent molecule or enzymes, including horseradish peroxidase (HRP), β-galactosidase, alkaline phosphatase, glucose oxidase, etc. Sufficient time is allowed for specific binding to occur again, then the slide is washed again to remove unbound conjugate and subject to detection by fluorescence or chemiluminescence detectors or a suitable substrate for the enzyme is added. Color is allowed to develop and the optical density is determined visually or instrumentally (measured at an appropriate wave length).

One assay for the EV analysis is an enzyme linked immunosorbant assay, i.e., an ELISA. Typically, in an ELISA, the peptidic probe of the invention is bound to the surface of a microtiter well directly or through a capture matrix (i.e., antibody, polymer coating, streptavidin/biotin). Residual, non-specific protein-binding sites on the surface are then blocked with an appropriate agent, such as bovine serum albumin (BSA), a buffered solution of nonfat dry milk. The well is then incubated with a biological sample likely containing EVs. The sample can be applied neat, or more often it can be diluted, usually in a buffered solution which contains a small amount (0.1-5.0% by weight) of protein, such as BSA and detergent such as Tween 20. After incubating for a sufficient length of time to allow specific binding to occur, the well is washed to remove unbound material and then incubated with an optimal concentration of an appropriate antibody (e.g., for specific EV markers such as CD9, CD63, CD81) that is conjugated to an enzyme or other label by standard procedures and is dissolved in blocking buffer. The label can be chosen from a variety of enzymes, including horseradish peroxidase (HRP), β-galactosidase, alkaline phosphatase, glucose oxidase, etc. Sufficient time is allowed for specific binding to occur again, then the well is washed again to remove unbound conjugate, and a suitable substrate for the enzyme is added. Color is allowed to develop and the optical density of the contents of the well is determined visually or instrumentally (measured at an appropriate wave length).

In another embodiment of the invention, the assay described above is performed in liquid, using beads, comprising magnetic beads, where peptidic probes of the invention are bound In one embodiment of an ELISA, a peptidic probe of the invention is immobilized on a surface, such as a ninety-six-well ELISA plate or equivalent solid phase that is coated with streptavidin or an equivalent biotin-binding compound at an optimal concentration in an alkaline coating buffer and incubated at 4° C. overnight. After a suitable number of washes with standard washing buffers, an optimal concentration of a biotinylated form of a composition/antigen of this invention dissolved in a conventional blocking buffer is applied to each well; a sample is added; and the assay proceeds as above.

Another useful assay format is a lateral flow format. The peptidic probe of the invention is immobilized on membrane, such as a PVDF (polyvinylidene fluoride) membrane (e.g. an Immobilon membrane (Millipore)) or a nitrocellulose membrane. When a solution of sample (blood, serum, etc) is applied to the sample application pad, it dissolves the labeled detection antibodies that bind to EV in the sample.

This mixture is transported into the next membrane (PVDF or nitrocellulose containing the peptidic probe) by capillary action. If EVs are present, they bind to the peptidic probe striped on the membrane generating a signal. An additional antibody specific to the colloidal gold labeled antibody (such as goat anti-mouse IgG) is used to produce a control signal.

It should be understood by one of skill in the art that any number of conventional assay formats, particularly immunoassay formats, may be designed to utilize the isolated peptidic probes of this invention for the detection of EVs. This invention is thus not limited by the selection of the particular assay format, and is believed to encompass assay formats that are known to those of skill in the art.

Other useful assay formats include the filter cup and dipstick. In the former assay, peptidic probes of the invention is fixed to a sintered glass or membrane filter to the opening of a small cap. The biological fluid or sample (e.g., about 5 mL) is worked through the filter. If the EV is present it will bind to the filter which can then be visualized through a second antibody/detector. The dipstick assay involves fixing an antigen or antibody to a filter, which is then dipped in the biological fluid, dried and screened with a detector molecule.

Other useful assay format include immobilization of peptidic probes of the invention into a hydrogel matrix such as a peptidic hydrogel, an agarose gel, or any polymeric o biopolymeric hydrogel and combination thereof. The biological fluid or sample is either mixed with the hydrogel matrix or contacted with it. If the EV is present, a peptidic probe-EV complex is formed and detected with any of the modalities reported above Much of the preceding discussion is directed to the detection of EVs in biological fluids. However, it is to be understood that the discussion also applies to the detection of EVs into any extracellular medium (for example cell lines or organoids culture media) and from pre-treated samples (i.e. samples subjected to EV isolation procedures such as size exclusion chromatography, ultracentrifugation etc)

In one aspect of the invention, a peptidic probe of the invention is associated with a carrier for EV isolation. The invention comprises contacting (incubating, reacting) a peptidic probe of the invention immobilized on the carrier with a sample of a biological fluid (e.g. cell culture supernatant, urine, saliva, serum or CSF) from a subject (e.g. human or other animal) or other source (e.g. microorganism or cell culture or vegetable extract) for capturing EVs. In the presence of EVs, a complex is formed and isolated from the solution.

Explanation will be given on an example by taking the case of using the magnetic particles, as the carrier pertaining to the present invention. First of all, a container, with the peptidic probe-carrier of the present invention as described above, is installed in a magnet stand, to collect the peptidic probe-carrier of the present invention on a tube wall using magnetic force, and the solution in the container is discarded. Next, the washing solution is added in the container, and stirred. The washing operation may be repeated several times, as necessary. A method for obtaining EVs of the present invention is characterized by comprising the following steps: (1) A step for forming a complex of the peptidic probe bound to the carrier, and the EV in the sample, (2) A step for separating the complex and the sample for example by magnetic force or centrifugation (3) A step for separating the EV from the complex to obtain the EVs In one format, the peptidic probe of the invention or a mixture of peptidic probes is conjugated to or mixed with self-assembling peptide hydrogelators. After mixing peptidic probe modified hydrogels with samples (for example serum containing EVs) and permeation of contaminants out from the hydrogel, EVs are trapped within functionalized hydrogels and detected by secondary antibodies or labelled peptidic probes of the invention.

In one format, after the steps described above, EVs are collected following release of the peptidic probe from the hydrogel or by reverting peptidic probe-EVs binding or by centrifugation.

In one format of the invention, the peptidic probe of the invention or a mixture of peptidic probes is conjugated to synthetic or natural polymers or a composition thereof, contacted with the sample containing EVs, after formation of the peptidic probe-EV complex, the polymer is subjected to centrifugation for pulling down the EVs In one format, after the steps described above, EVs are collected following release of the peptidic probe from the polymer or by reverting peptidic probe-EVs binding.

In one format of the invention, the peptidic probe of the invention or a mixture of peptidic probes is conjugated to synthetic or natural polymers or a combination thereof, contacted with the sample containing EVs, after formation of the peptidic probe-EV complex, the polymer is subjected to centrifugation for pulling down the Evs.

In one format of the invention, the peptidic probe of the invention or a mixture of peptidic probes is conjugated to a beaded chromatographic medium (e.g. an agarose or polyacrylamide gel); a fibrous cellulose matrix; an HPLC matrix; an FPLC matrix; a substance having molecules of such a size that the molecules with the peptidic probe bound thereto, when dissolved or dispersed in a liquid phase, can be retained by means of a filter. The carrier described above is contacted statically or under a flow with the sample containing EVs, the peptide-EV complex is formed and retained from the solution.

In one format, after the steps described above, EVs are collected following release of the peptidic probe from the carrier or by reverting peptidic probe-EVs binding.

One embodiment of the invention includes integration of EV isolation and analysis as described above in one platform/chip/device or kit.

Another embodiment is for isolation and/or release.

Peptidic probes—EVs association can be also directed reverted following a stimulus, leading to the release of the bound EVs. Stimuli that can be used to possibly revert binding are diverse, including but not limited to: pH, reducing agents, UV radiation, IR radiation, temperature, metals, ions, chelating agents, detergents, chemicals, and/or enzymes.

One embodiment of the invention includes appropriate linkers and methods to release EVs after capturing. A linker (spacer) can be a single amino acid (e.g., G (glycine)), an amino acid sequence or an organic residue, such as 3,6-dioxaoctanoic acid, amino hexanoic acid or others. Spacer can be both hydrophilic or hydrophobic, or have hybrid properties. Spacer can be cleavable, meaning it can be broken in one or more parts following a stimulus, leading to the release of the bound EVs. Stimuli that can be used to actuate spacer cleavage are diverse, including but not limited to: pH, reducing agents, UV radiation, IR radiation, temperature, metals, detergents, chemicals, and/or enzymes.

Another embodiment is for EV isolation, membrane modification (e.g., functionalization or decoration) and release.

In one embodiment of the invention, a peptidic probe of the invention bearing an optional functional moiety is associated with a carrier for EV isolation and used for integrated EV membrane decoration and isolation. An embodiment comprises contacting (incubating, reacting) a peptidic probe of the invention bearing the optional membrane decorating moiety (small molecule, peptide, DNA/RNA sequence, protein) and immobilized on the carrier with a sample of a biological fluid (e.g. cell culture supernatant, urine, saliva, blood or CSF) from a subject (e.g. human or other animal) or other preparation of EVs from various sources (e.g. microorganism or cell culture or vegetable extract or blood bags) for capturing and decorating EV membranes. In the presence of EVs, a complex is formed and isolated from the solution.

In one format, after the steps described above, modified EVs (or decorated EVs or functionalized EVs) are collected following release of the peptidic probe from the carrier or by reverting peptidic probe-EVs binding.

One embodiment of the invention includes integration of EV modification, decoration and isolation as described above in one platform/chip/device or kit.

Kits and Methods of Using Kits

Kits are known in the art, and a wide variety of kits with different components described herein and instructions and containers for use of the kits can be carried out.

One embodiment of the invention is constituted by kits for EVs analysis, which comprises one or more peptidic probes of the invention, one or more compositions of the invention, and optionally comprises one or more additional peptidic probes. The peptidic probe(s) may comprise a detectable label, or the kit may include a detection system (e.g. a labeled conjugate and a reagent; or beads comprising unique spectral signatures) for detecting EVs which bound to the peptidic probe. In one embodiment, the kit can contain a substrate (e.g., solid or semi-solid) for immobilizing the peptide, such as a microarray slide, a microwell plate, an Immobilon or nitrocellulose membrane, resin, magnetic beads, latex beads, or polystyrene beads, and buffer solutions to be used to run the experiment.

The kit can include one or more of the EV isolation formats described above (beads, polymer, hydrogel etc) integrated with one of the EV detection format described above (microarray, ELISA, etc), another appropriate assay device, various diluents and buffers, labeled conjugates or other agents for the detection of specifically bound EVs, and other signal-generating reagents, such as antibodies, enzyme substrates, cofactors and chromogens. Other components of a kit can easily be determined by one of skill in the art.

In one embodiment, a kit comprises buffers or other reagents appropriate for constituting a reaction medium allowing the formation of a peptidic probe-EV complex. Such kits provide a convenient, efficient way for a research laboratory to analyse EVs.

Reagents for microarrays, ELISA or other assays according to this invention can be provided in the form of kits. Such kits are useful for detecting EVs contained in a sample. Such EV analysis kits can contain a peptidic probe of the invention (and, if desired, additional peptidic probes as discussed above) and, optionally, a system for (means enabling) detection of a peptidic probe of the invention bound to EVs, and/or a surface to which the peptidic probe can be bound. In one embodiment, a kit contains a mixture of suitable peptidic probes or means for preparing such mixtures, and/or reagents for detecting peptidic probe-EV complexes.

The kit can include microarray slides or chips or microtiter plates or beads to which the peptidic probe(s) of the invention have been bound, another appropriate assay device, various diluents and buffers, labeled conjugates or other agents for the detection of specifically bound EVs, and other signal-generating reagents, such as antibodies, enzyme substrates, cofactors and chromogens. Other components of a kit can easily be determined by one of skill in the art. Such components may include coating reagents, polyclonal or monoclonal antibodies, or a cocktail of two or more of the antibodies, purified or semi-purified EVs as standards, detector antibodies, an anti-mouse or anti-human antibody with indicator molecule conjugated thereto, an ELISA plate prepared for absorption, indicator charts for colorimetric comparisons, disposable gloves, decontamination instructions, applicator sticks or containers, a sample preparatory cup, etc. In one embodiment, a kit comprises buffers or other reagents appropriate for constituting a reaction medium allowing the formation of a peptidic probe-EV complex. Such kits provide a convenient, efficient way for a research laboratory to analyse EVs.

Kits for conducting this or other assay methods, using detection antibody or other specific binding partner of the invention and assay medium are also included in the invention. Other components of a kit can easily be determined by one of skill in the art.

One embodiment of the invention is a kit for EVs isolation, which comprises one or more peptidic probes of the invention, or one or more compositions of the invention, and optionally comprises one or more additional peptidic probes and buffer and solutions for capturing and release of EVs.

In one embodiment, a kit comprises at least one buffer optionally with other reagents appropriate for constituting a reaction medium allowing the formation of a peptidic probe-EV complex for EV membrane modification or decoration. Such kits provide a convenient, efficient way for integrated modification or decoration along with isolation.

Working Examples

The following non-limiting working examples are included to illustrate further various embodiments. It should be appreciated by those of skill in the art that the techniques disclosed in the examples that follow represent techniques discovered to function well in the practice of the claimed methods, compositions and apparatus. However, those of skill in the art should, in light of the present disclosure, appreciate that many changes may be made in the specific embodiments which are disclosed and still obtain a like or similar result without departing from the spirit and scope of the invention.

Preparation of Peptidic Probes Derived from Bradykinin

Bradykinin peptide (BK) is a cationic peptide ligand (sequence: RPPGFSPFR) that was selected as a core molecule or sequence in this example for the following reasons. It is reported that BK and some of its derivatives display a selective affinity to highly curved vesicle surfaces, particularly when displayed in a multivalent trimeric form [22]. Previously generated knowledge suggests that BK populates non-structured conformations in aqueous solutions but undergoes conformational modifications upon interaction with membrane lipids, which allows the accumulation of the active peptide conformation in highly anionic vesicles. Other findings suggest that an increase in the local peptide concentration at the vesicle surface is not only due to the cationic arginine at positions 1 and 9 but also due to the phenylalanine at positions 5 and 8, supporting electrostatic and hydrophobic-driven peptide lipid interaction. These two properties are deemed to facilitate differentiating phospholipid composition of vesicles. Proline residues induce a B-turn conformation that orients the Arginine residues on the same face of the peptide to a claw-like shape. According to literature reports, this conformation is believed to be important for lipid recognition and attachment [18-21].

Herein, the previously reported BK sequence was re-designed in a suitable form for its site-selective conjugation to different supports and surfaces. Lysine and glycine residues were added as spacers and also to enable sequence ramification (branching) at lysine position by extending the peptide sequence starting from both lysine amino groups (See FIGS. 1 and 2).

An extra polyethylene glycol spacer molecules was also incorporated (FIG. 1). A terminal propargyl glycine residue was also added to enable click chemistry mediated conjugation to a support [23,24]; alternatively, a cysteine residue was incorporated for subsequent functionalization with biotin or fluorescent probes. The same general scheme was applied to synthetize one linear (BP) and two multivalent peptidic probes, one branched (BPb) probe and one tandem (BPt) probe. (FIG. 2). A scrambled peptide sequence (BPs) and a mutated sequence (BPm) were also produced. Finally, given the key role of electrostatic interactions in initiating the complex membrane-sensing mechanism reported for BK, a negative control peptide was also synthesized where arginine residues were mutated to (oppositely charged) glutamic acid residues (BPn). All the sequences are reported in FIG. 1.

All the peptidic probes reported in FIG. 1 were synthesized using standard Fmoc chemistry and microwave-assisted solid phase peptide synthesis on Rink amide resin. Sequences were assembled using a Oxyma/DIC mixture as activators for the coupling steps. The N-terminus was deprotected using 20% piperidine in DMF. DMF was used for post-coupling and post-deprotection washings. Peptidic probes were cleaved from the resin using 92.5/2.5/2.5/2.5 TFA/TIS/$H_2O$/Thioanisole mixture, purified by reverse phase HPLC, lyophilized, and characterized by mass spectrometry.

Example 1: Capturing and Analysis on SP-IRIS Chips of EVs from HEK Cell Line and from Human Serum

Peptides Microarrays

Peptides were first dissolved in DMSO to 1 mM stock solution and then diluted to the final spotting concentration (100 μM) into the printing buffer for CuACC conjugation on Copoly Azide coated surfaces (5 mM Na/Acetate pH 4.8, 50 mM Trehalose, 100 μM CuSO4, 400 μM THPTA and 6.25 mM Ascorbic Acid). Patterned silicon chips with 80 nm $SiO_2$ layer, suitable for SP-IRIS by the ExoView™ platform, were arrayed with 5 replicated spots of peptides via CuAAC mediated chemoselective immobilization. Microarrays were arrayed on Copoly Azide-coated patterned silicon chips [23,24], with 80 nm oxide layer thickness, using a non-contact S12 Spotter (Scienion Co., Berlin, Germany), depositing 1 drop for each spot.

Printed chips were placed in a humid chamber and incubated overnight at room temperature.

The following day, chips were immersed in a filtered 2 mM EDTA water solution for 1 h, then washed with Milli-Q water.

Microarrays were characterized by quantifying the immobilization density of peptides and according to previous findings [23] [24] the average binding yield of each peptide was 1.5-3.5 ng/mm$^2$.

As a first experimental set to probe peptide-based EVs capturing, EVs were first isolated from HEK (Human embryonic kidney) cells by ultracentrifugation (UC).

Isolation of HEK EVs by Ultracentrifugation

Three days conditioned media from HEK cells were harvested and centrifuged at 500 g for 25 minutes. Supernatants were filtered with 0.22 mm filters (Merck Millipore) and centrifuged in a Sorvall™ WX Ultracentrifuge (ThermoFisher Scientific, WX Ultra 100 #75000100) at 150.000 g for 90 minutes at 4° C. with a SureSpin™ 630 swinging bucket rotor (ThermoFisher Scientific) to pellet EVs. After supernatant was carefully removed, EVs-containing pellet were resuspended in PBS and stored at −80° C. until use.

Figure 3:
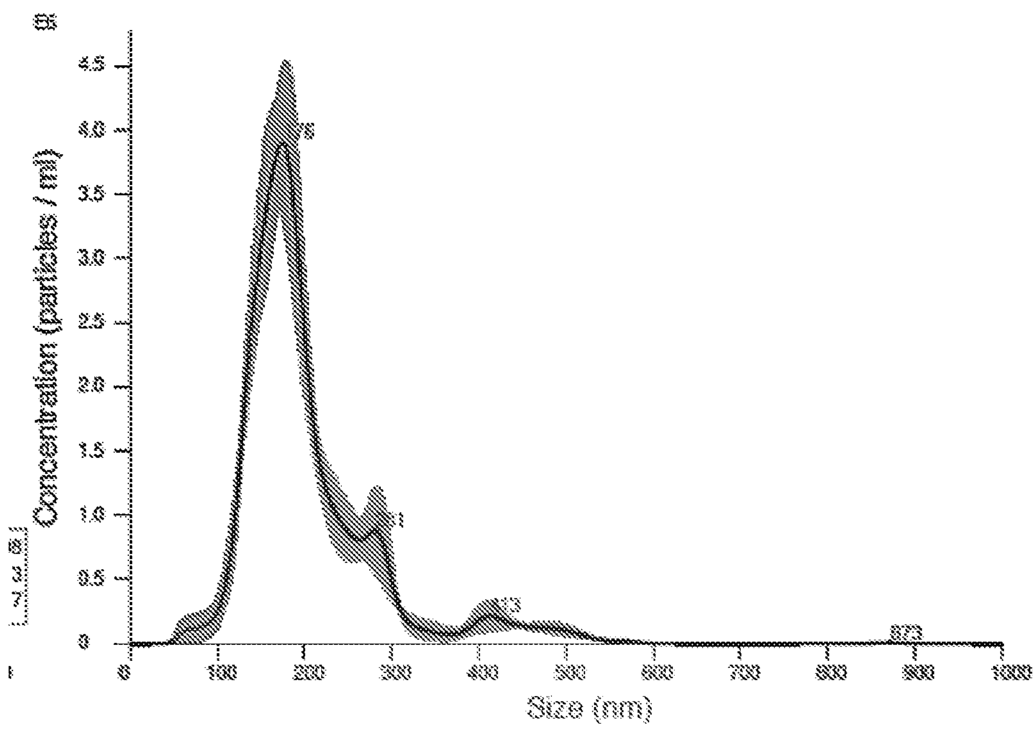
FIG. 3: NTA analysis of the HEK UC isolated sample. NTA provided a mean particle size of 203±3 nm and a concentration of $3.94\times10^9$ particles/mL.
Figure 4:
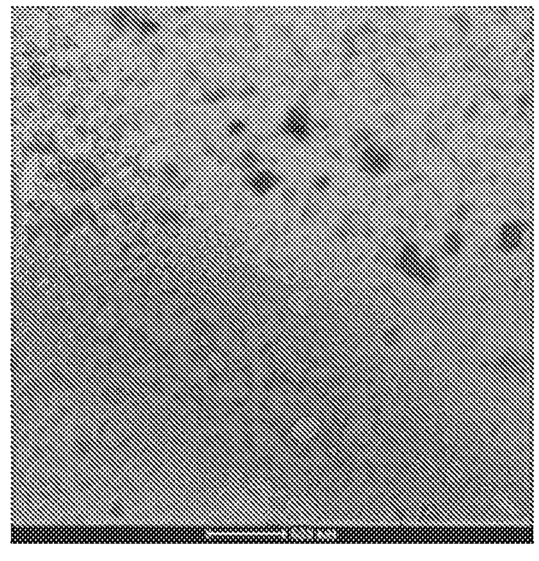
FIG. 4: TEM imaging of the HEK UC isolated sample
Figure 5:
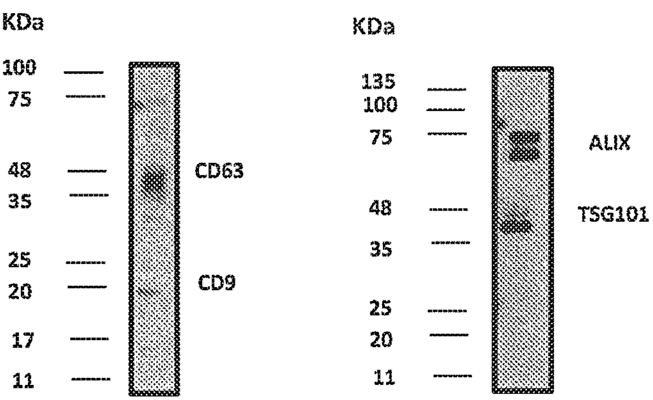
FIG. 5: Western Blot analysis of the HEK UC isolated sample. The presence of the transmembrane proteins CD9 and CD63 and the luminal proteins ALIX and TSG101 is verified.

HEK UC sample was characterized according to MISEV2018 guidelines [25], by Nanoparticle Tracking Analysis (NTA), Transmission Electron Microscopy (TEM) and Western blotting (WB) to demonstrate the presence of EV membrane and luminal proteins. Results confirmed the presence of vesicles with size, morphology and protein content compatible with EVs (FIGS. 3-5).

Nanoparticle Tracking Analysis (NTA)

Nanoparticle tracking analysis (NTA) was performed according to manufacturer's instructions using a NanoSight NS300 system (Malvern Technologies, Malvern, UK) configured with 532 nm laser. All samples were diluted in filtered PBS to a final volume of 1 ml. Ideal measurement concentrations were found by pre-testing the ideal particle per frame value (20-100 particles/frame). The following settings were set according to the manufacturer's software manual. A syringe pump with constant flow injection was used and three videos of 60 s were captured and analysed with NTA software version 3.2. From each video, the mean, mode, and median EVs size was used to calculate samples concentration expressed in nanoparticles/mL.

Transmission Electron Microscopy (TEM)

Isolated EVs were absorbed on glow discharged carbon coated formvar copper grids, washed with water, contrasted with 2% uranyl acetate and air-dried. Grids were observed with a Zeiss LEO 512 transmission electron microscope. Images were acquired by a 2 k×2 k bottom-mounted slow-scan Proscan camera controlled by EsivisionPro 3.2 software.

Western Blot Analysis

Purified EVs were resuspended in not reducing Laemmli buffer for the detection of CD9 and CD63, in reducing buffer for ALIX and TSG101 and boiled for 5 minutes at 95° C. Proteins were resolved by SDS-PAGE and electro-transferred onto a nitrocellulose membrane. Nonspecific sites were blocked with 5% (w/v) skimmed milk in T-TBS (Tris-buffered saline: 150 mM NaCl, 20 mM TrisHCl, pH 7.4, and 0.5% Tween 20). Membranes were incubated overnight at 4° C. with the following antibodies: mouse anti-CD9 (1:5000, BD Pharmingen, #555370, San Jose, CA, USA), mouse anti-CD63 (1:20000; BD Pharmingen, #556019, San Jose, CA, USA), mouse anti-ALIX (1:500, Santa Cruz, #sc-271975, Santa Cruz, CA, USA) and mouse anti-TSG101 (1:500, Novus Bio, #NB200-112, Littleton, CO, USA). After washing with T-TBS, membranes were incubated with goat anti-mouse (1:10000-1:50000) IgG conjugated to horseradish peroxidase for 45 min. Positive immunoreactive bands were detected by the enhanced chemiluminescence method (Immobilon™ HRP substrate, #WBKLS0500, Millipore Corp., Billerica, MA, USA).

Based on NTA quantifications, serial dilutions of the HEK UC sample in the $1\times10^6$-$1\times10^9$ particles/mL range were prepared in PBS, filtered by a 200 μm filter, and incubated for 150 minutes on peptide chips. EV samples were in static conditions on the printed chips in a humid chamber. EV label-free analysis were carried out using a nScan2 reader (NanoView Biosciences, Boston, MA). The reader automatically acquires interferometric images of the microarray. NanoViewer 2.6.0 software counts nanoparticles captured on the peptide spots within a user defined particle contrast. For EV analysis, the size window was selected as 1-30% to include particle sizes from 50-200 nm.

Figure 6:
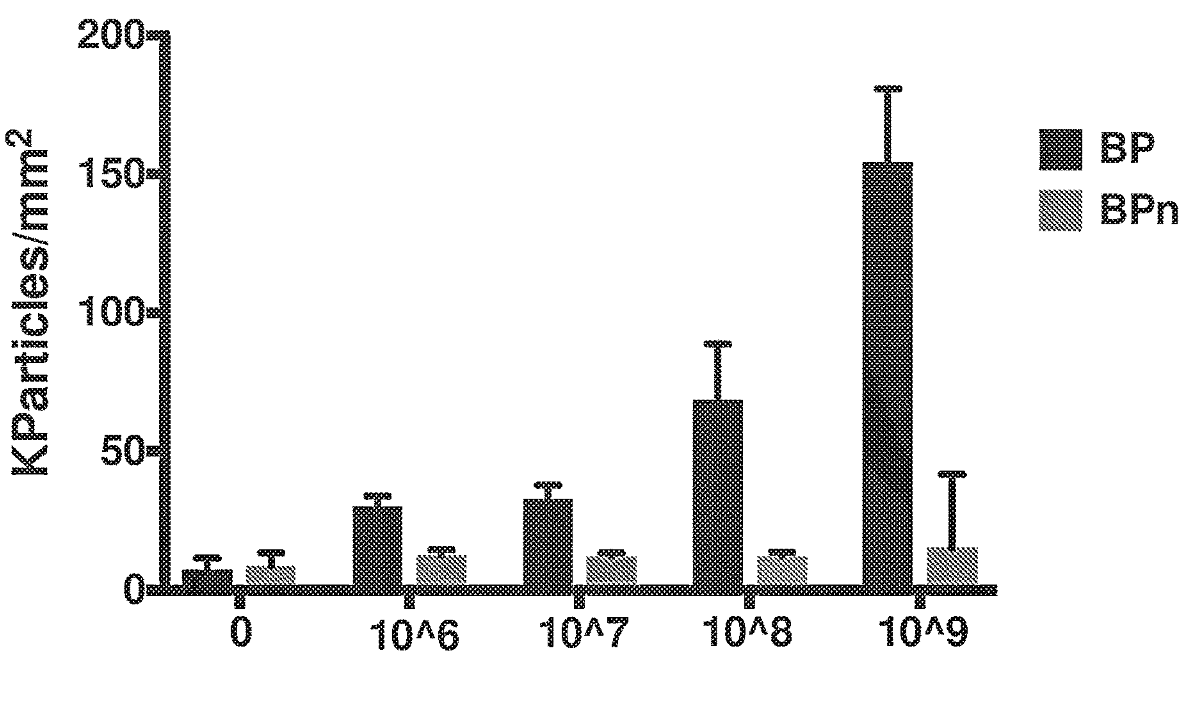
FIG. 6: HEK UC particle density per $mm^2$ detected on BP and BPn peptide spots in a blank sample (filtered PBS) and in $1\times10^6$-$1\times10^9$ EV/mL concentrations range. A clear dose-response effect is visible. Signal on BPn peptide is negligible
Figure 7:
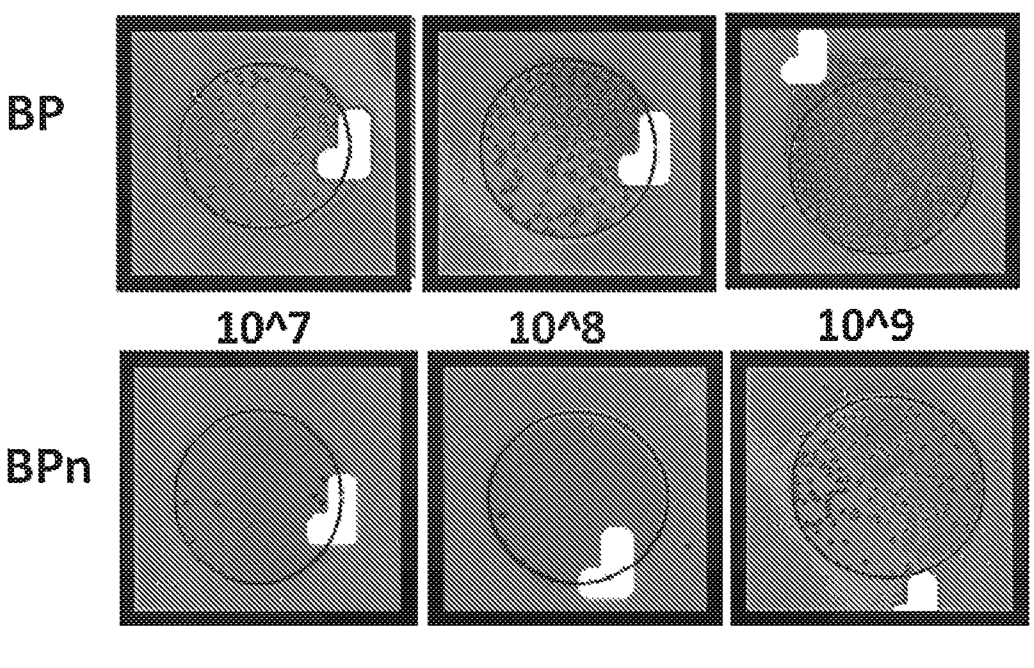
FIG. 7: representative spot images for the BP and BPn peptides. Grey dots indicates detected particles.
Figure 8:
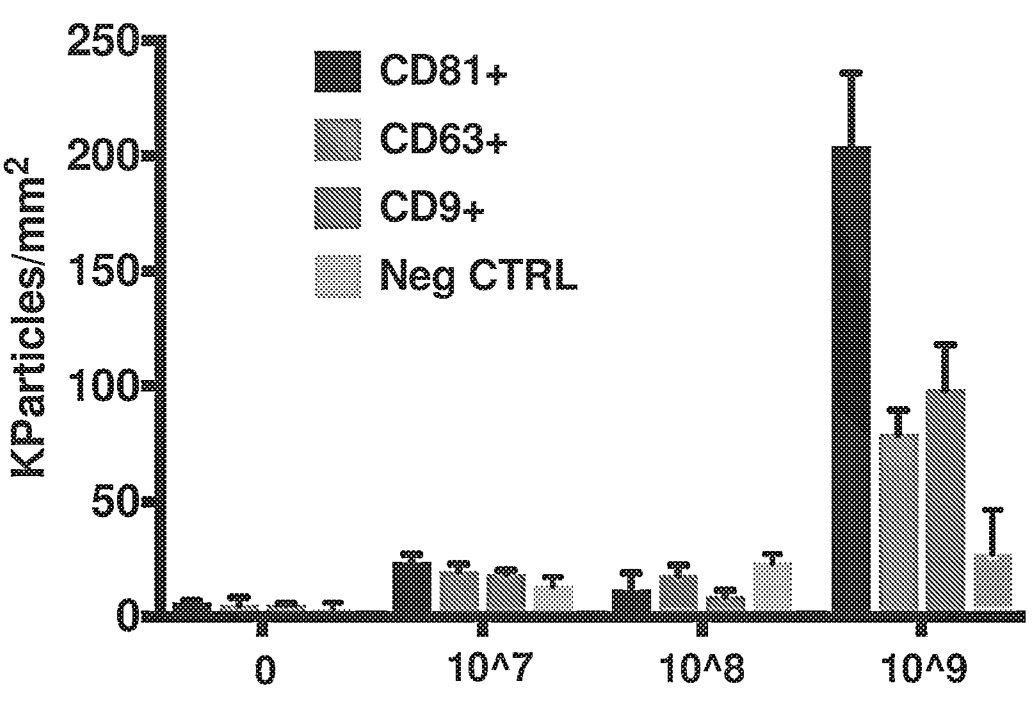
FIG. 8: HEK UC particle density per $mm^2$ detected on antibody microarray (anti CD81/CD63/CD9). Only $1\times10^9$ particles/mL concentration is distinguishable from the negative control antibody

Net values of detected EVs on BP and BPn from five spot replicates were averaged and reported as kiloparticles/square millimeter (FIG. 6). Notably, we could immediately assess that a significant amount of nanoparticles (grey dots) could be detected within the area of BP spots (FIG. 7), whilst negligible binding was observed for the negative control peptide BPn at the various concentrations. Moreover, microchips incubation with different sample concentrations highlighted a dose-response effect, with detected particle signal on BP being clearly distinguishable down to $1\times10^7$ particles/mL concentration (FIG. 6). Notably, when the same serial dilutions of the HEK UC sample ($1\times10^6$-$1\times10^9$ particles/mL) were incubated on chips spotted with anti-tetraspanins antibodies (anti CD81/CD63/CD9), provided by NanoView Biosciences (Boston MA), only the highest concentration ($1\times10^9$ particles/mL) provided a distinguishable counting from the non-specific signals detected on the negative antibody control (FIG. 8). Of note, the average particle counting detected on the antibody spots was lower than that provided by BP for each tested HEK UC sample.

Figure 9:
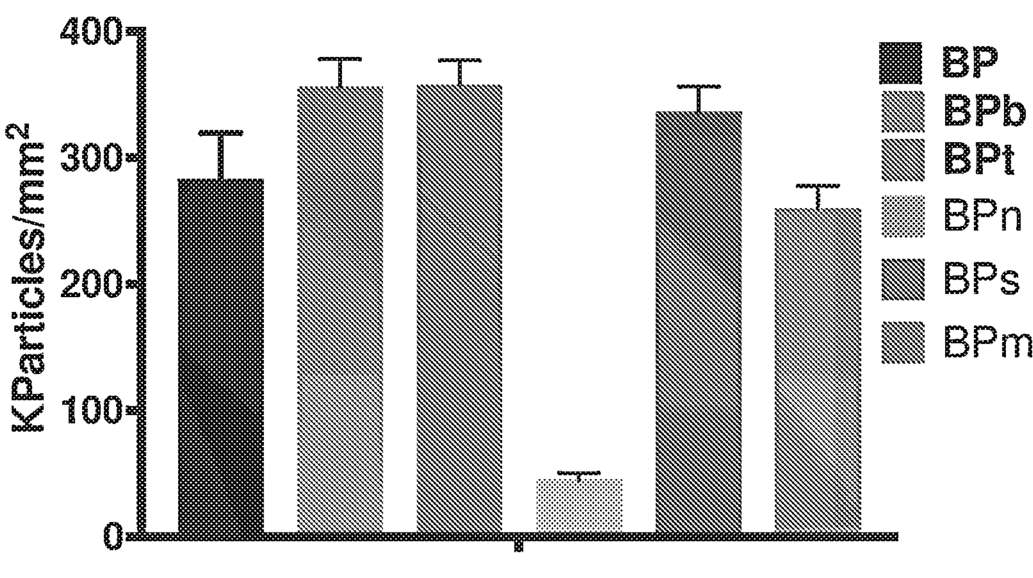
FIG. 9: Particle density per $mm^2$ detected on BP and multivalent BPb and BPt peptides when incubated with $1\times10^9$ particles/mL HEK UC sample.
Figure 10:
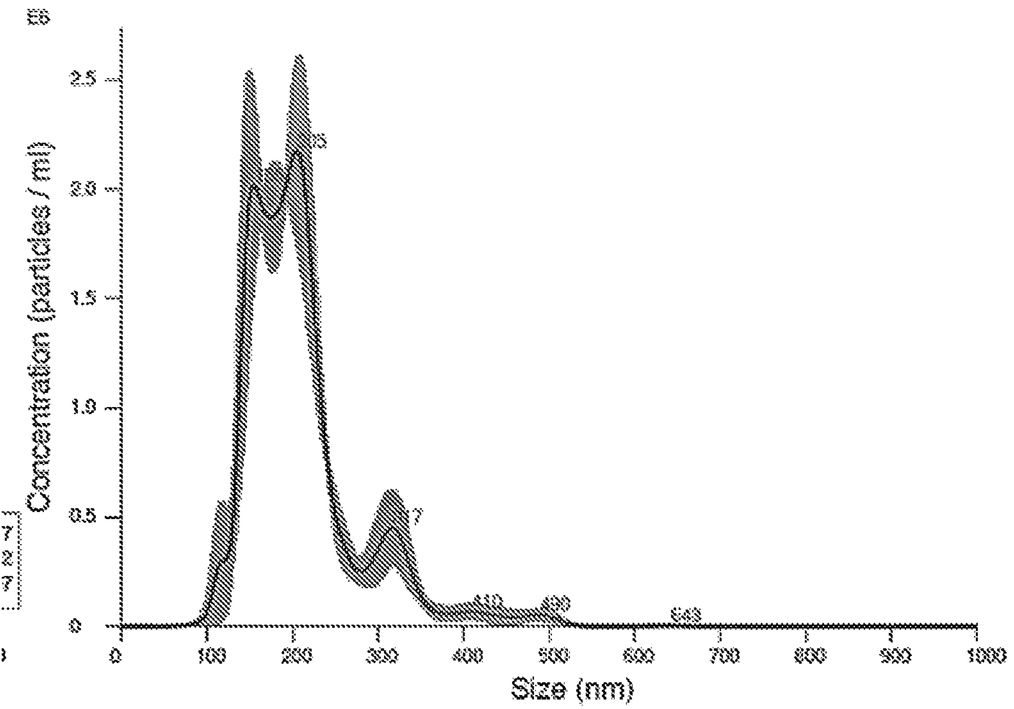
FIG. 10: NTA analysis of the serum UC sample. NTA provided a mean particle size of 210±2.5 nm and a concentration of $1.23\times10^9$ particles/mL.
Figure 11:
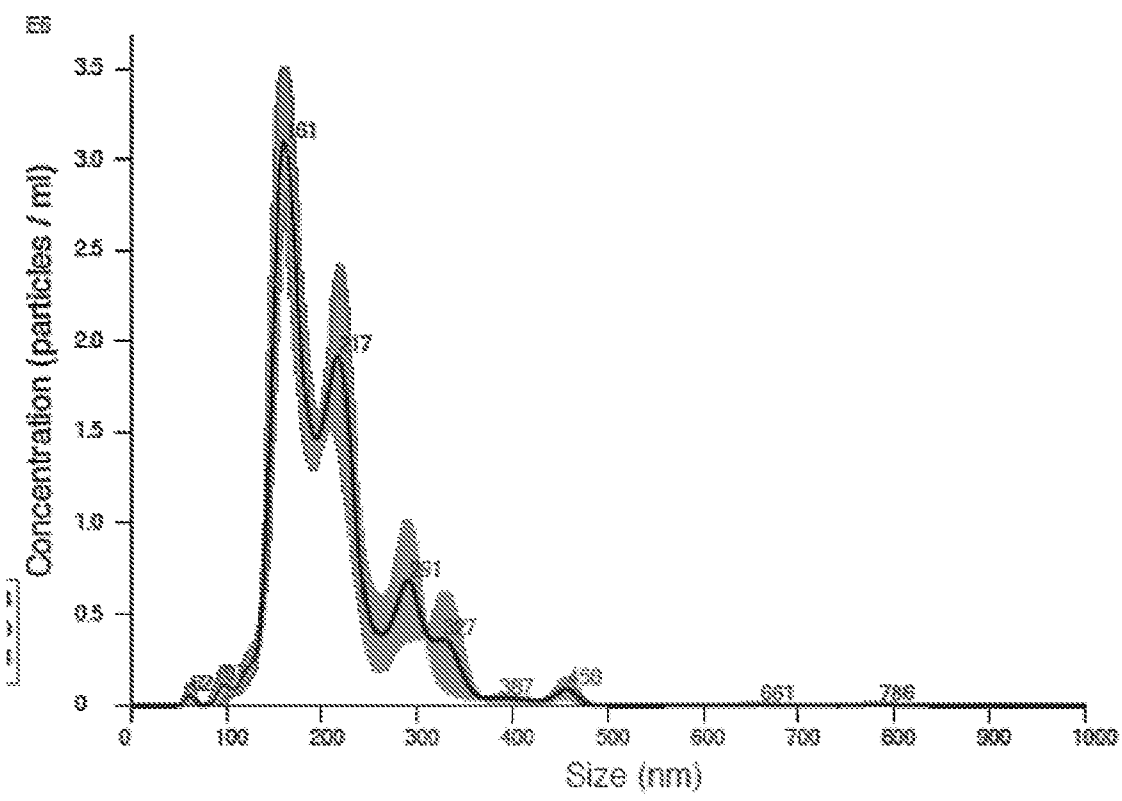
FIG. 11: NTA results of the analysis of the SEC isolated sample from serum. NTA provided a mean particle size of 208±2.3 nm and a concentration of $1.27\times10^9$ particles/mL.
Figure 12:
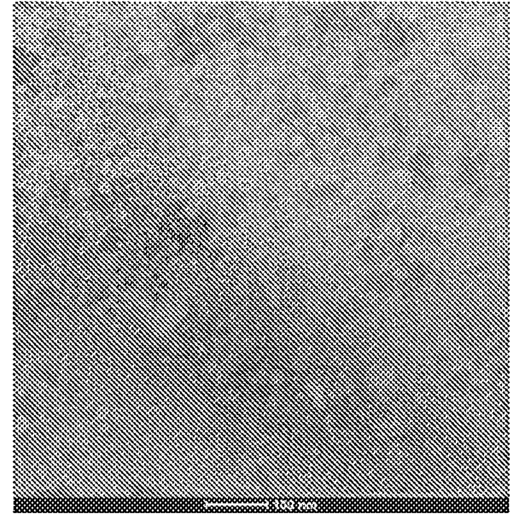
FIG. 12: TEM imaging of the UC sample. from human serum
Figure 13:
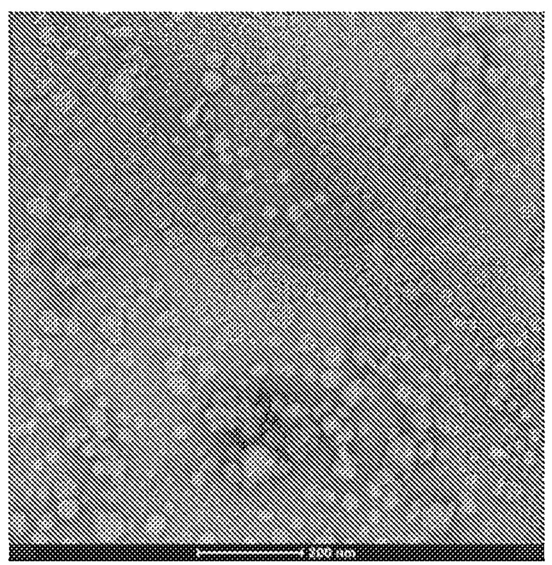
FIG. 13: TEM imaging of the SEC samples.
Figure 14:
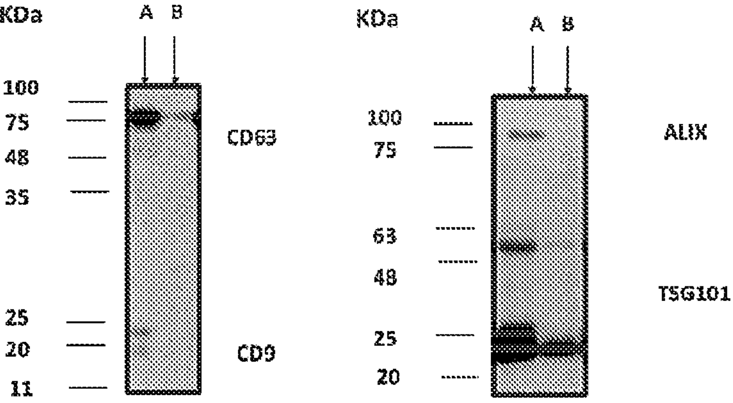
FIG. 14: Western Blot analysis of the UC (A) and SEC (B) isolated samples from human serum. The presence of the transmembrane proteins CD9 and CD63 and the luminal proteins ALIX and TSG101 is checked. The UC (A) sample is positive for CD63, CD9; ALIX and TSG101. The SEC (B) sample is positive to CD63 and TSG101.

BP, BPb, BPt, BPs and BPm showed particle capturing ability. As for the multivalent peptide forms BPb and BPt, only a slight increase in vesicle binding was observed (FIG. 9). This is in apparent contradiction with the enhancement of EVs binding observed for BK-tri [22], but this finding could be actually ascribed to the inherent multivalency of the chip surface towards the vesicle membrane. Indeed, due to the difference in size, many peptides probes protruding out of the chip surface are possibly or likely cooperatively involved to the binding of a single vesicle. With this purified EV sample, peptides BPs and BPm provided and EV capturing efficiency comparable to that of BP peptide (FIG. 9). In any tested case, peptides provided a capturing capacity higher than antibodies anti CD81, CD63, CD9.

BP capturing of EVs from human serum was assessed testing the peptide microarray with vesicles purified from a pool of serum samples by two common EV isolation procedures: ultracentrifugation (UC) and Size Exclusion Chromatography (SEC). Samples were characterized by NTA, TEM and WB (FIGS. 10-14).

Serum Separation

Four mL of blood were collected in BD VACUTAINER (clot activator tube). Serum samples were separated after centrifugation within two hours from blood collection at 1900 g for 10 minutes at 4° C. Serum samples from 5 healthy controls were pooled and frozen at −20° C. until use.

Serum UC: 1 mL of serum pool was filtered with 0.22 mm filters (Merck Millipore) diluted 1:1 with PBS and centrifuged in a Optima™ TLX Preparative Ultracentrifuge, Beckman Coulter™ at 150.000 g for 120 minutes at 4° C. with a TLA-55 Rotor (Beckman Coulter™) to pellet EVs. After supernatant was carefully removed, EVs-containing pellet were stored at −80° C. until use.

SEC was performed according to the manufacturer's instructions of the qEV single column (Izon, Christchurch, New Zealand). Briefly, after column equilibration with PBS, 150 μL of the pool of sera were loaded, 200 μL were collected; the first 5 fractions (F1-F5) were discarded. The seventh fraction (F7) that according to the manufacturer represents the fraction with the highest amount of vesicles was used for analysis and trypsin treatment.

Figure 15:
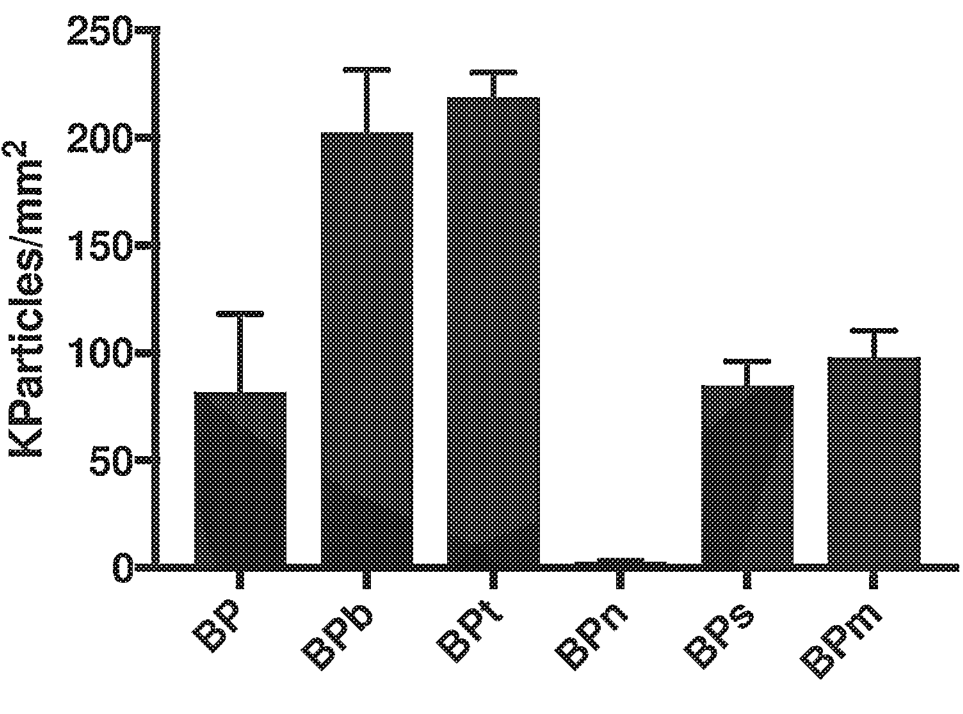
FIG. 15: Label free counting of EVs for the UC isolated sample from human serum on the BP peptides.

For the UC sample, label free counting on BP peptides was performed providing results analogous to those provided by the UC HEK sample (FIG. 15) thus demonstrating wide applicability of BP ligands with different isolation protocols. Notably, in these serum derived samples, the multivalent BPb and BPt peptides provided a clearly improved capturing capacity compared to BP (FIG. 15).

Figure 16:
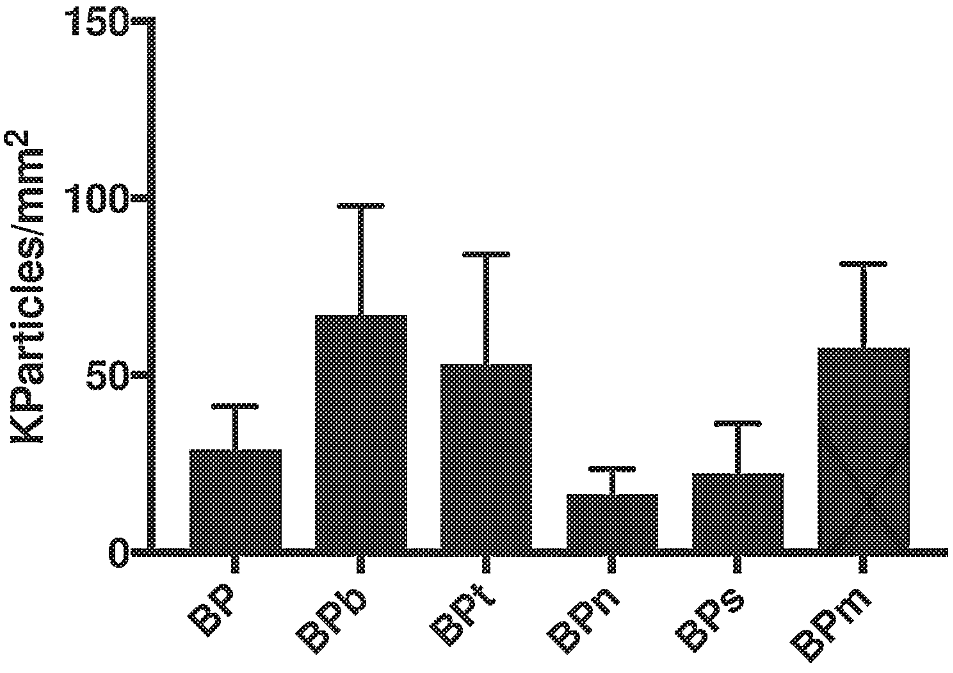
FIG. 16: Label free counting for the SEC isolated sample from human serum on the BP peptides.

For the SEC sample, label free counting on BP peptides was performed providing results analogous to those provided by the UC HEK sample (FIG. 16). However, in these serum derived samples, the multivalent BPb and BPt peptides provided a dramatic improvement of capturing capacity compared to BP and BPm and BPs (FIG. 16).

Figure 17:
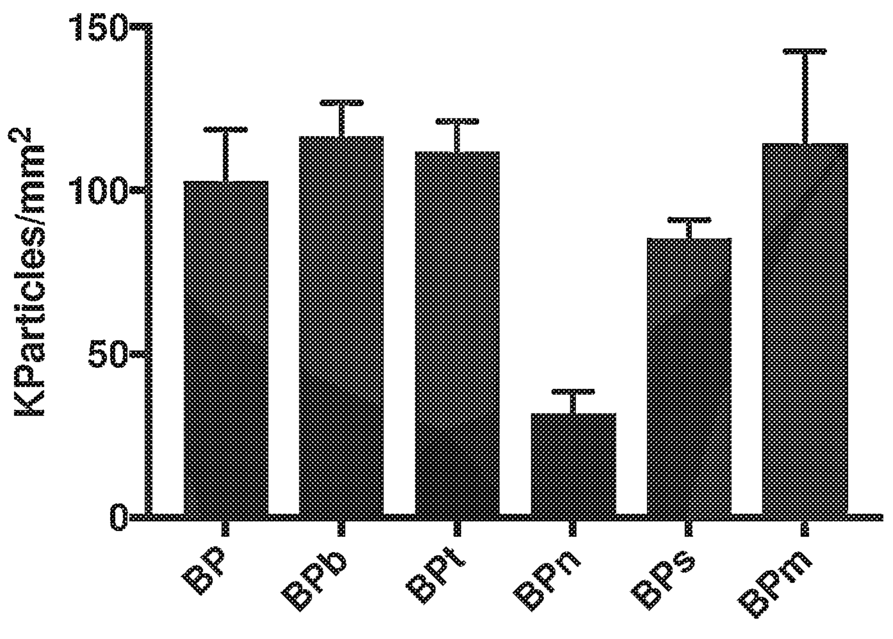
FIG. 17: Label free counting for vesicles from unpurified human serum on the BP peptides.

In addition to isolated vesicles, peptide ligands were tested with pure serum. An isolation-free workflow is indeed a highly desirable feature to get unbiased EVs analysis. The pooled sera sample was just filtered by a 0.2 μm syringe filter, diluted 1:10 in PBS and incubated on a chip arrayed with the BP peptides. In accordance to previous results on UC and SEC samples, particles from untreated serum were label free detected on all peptides; the negative control BPn provided a particle density slightly higher compared to results obtained with isolated samples (FIG. 17).

To assess the role of peptide exposure upon surface on the efficiency of EVs capturing, we compared a nonspecific (random) immobilization on nucleophile-reactive polymer-coated chips versus a chemoselective peptides binding to provide predetermined probes orientation. Of note, both strategies rely on the same polymer for chips coating (MCP-2, Lucidant Polymers), that can be differently functionalized to introduce selectively reactive handles (Copoly Azide) [24] for click-type peptide immobilization.

Figure 18:
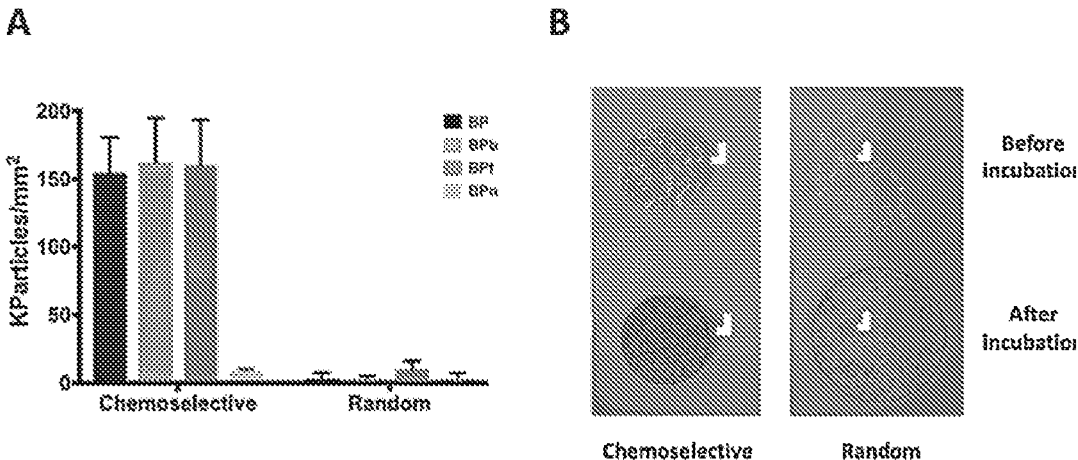
FIG. 18; A: EV density on BP peptides immobilized either chemoselectively on Copoly Azide or randomly on MCP-2. EV capturing capacity is abolished when peptides are not oriented on the microarray surface. B: comparison of a representative images of BP spot either chemoselectively or randomly immobilized. Spot size is smaller on copoly Azide, edges well defined and particle counting after incubation higher.

Peptide microarrays were incubated with SEC isolated EVs from serum ($1\times10^9$ particles/mL). Remarkably, the EV binding capacity of BP peptides was totally abolished when peptides were not properly oriented by a site-selective surface immobilization strategy (FIGS. 18A and 18B), demonstrating the important role of surface orientation.

Figure 19:
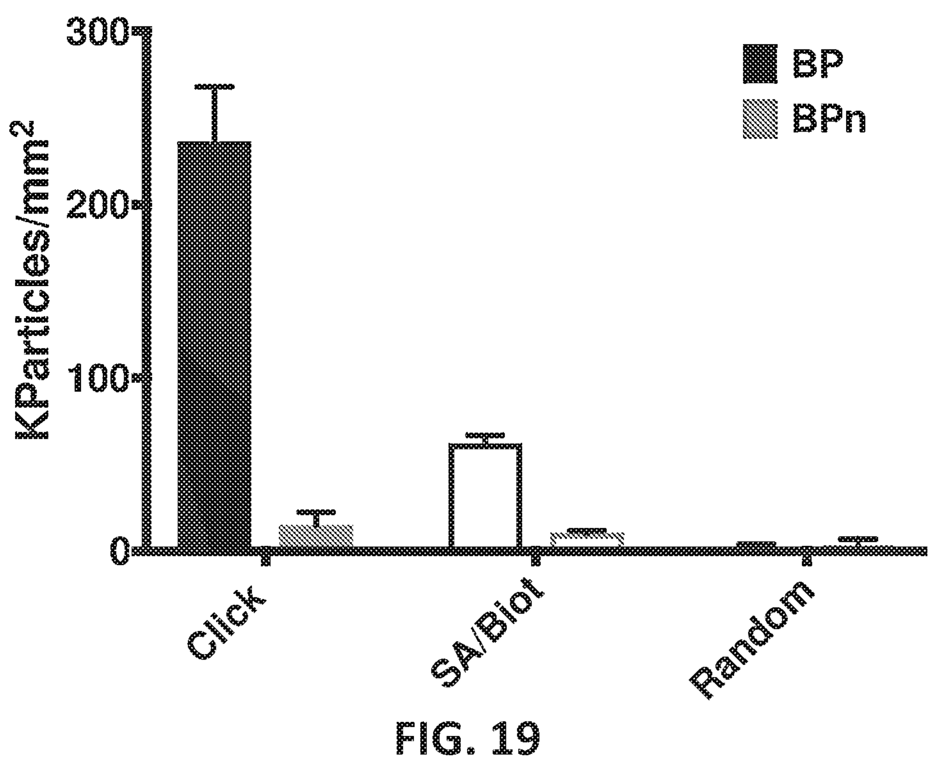
FIG. 19: comparison of binding capacity of the SEC isolated EVs from human serum ($1\times10^9$ particles/mL) incubated on BP and BPn immobilized by click chemistry, via streptavidin/biotin and by random immobilization

To provide additional insights on the general feasibility of this approach, peptide surface orientation was also accomplished by the well known biotin-streptavidin system, using biotinylated-BP peptide immobilized on streptavidin spotted on MCP-2 that though less efficient than click-type immobilization, maintained EVs binding capacity (FIG. 19). In this case, streptavidin was spotted at the concentration of 1 mg/mL in PBS on MCP-2 slides, following blocking with BSA 1% w/V in PBS, the slide was incubated for 60 min with 100 uM biotinylated BP to allow oriented immobilization. In the case of random immobilization of BP, 100 uM peptide in PBS was spotted on MCP-2 coated slide.

Figure 20:
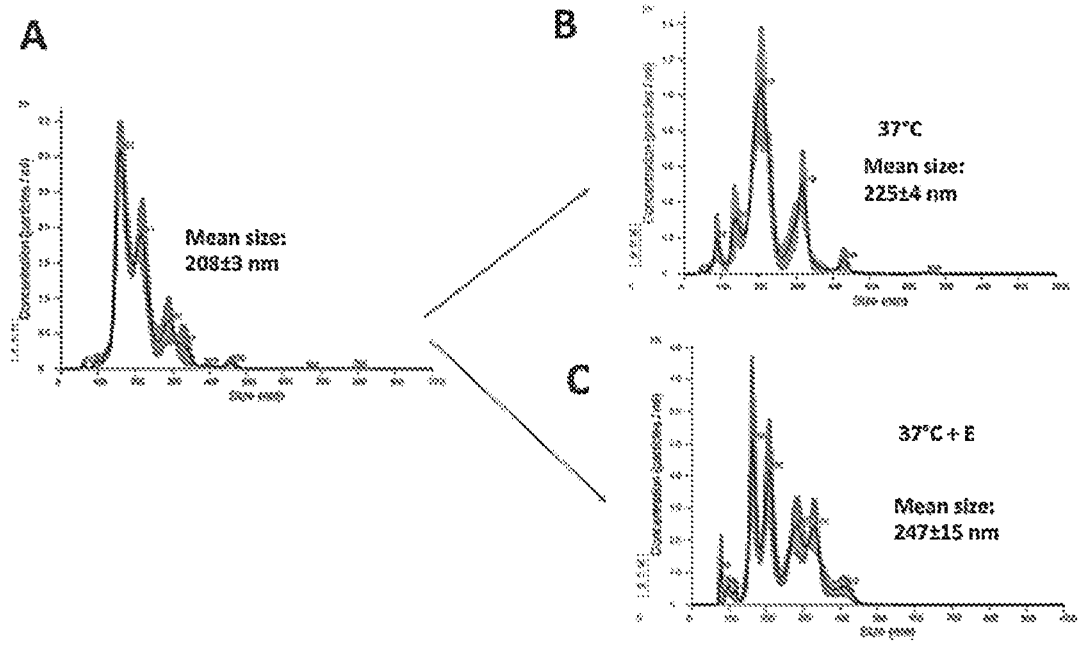
FIG. 20: A: SEC isolated EVs from human serum characterized before treatment; B: after 6 hours incubation at 37° C. without enzyme; C: after 6 hours incubation at 37° C. in presence of trypsin.
Figure 21:
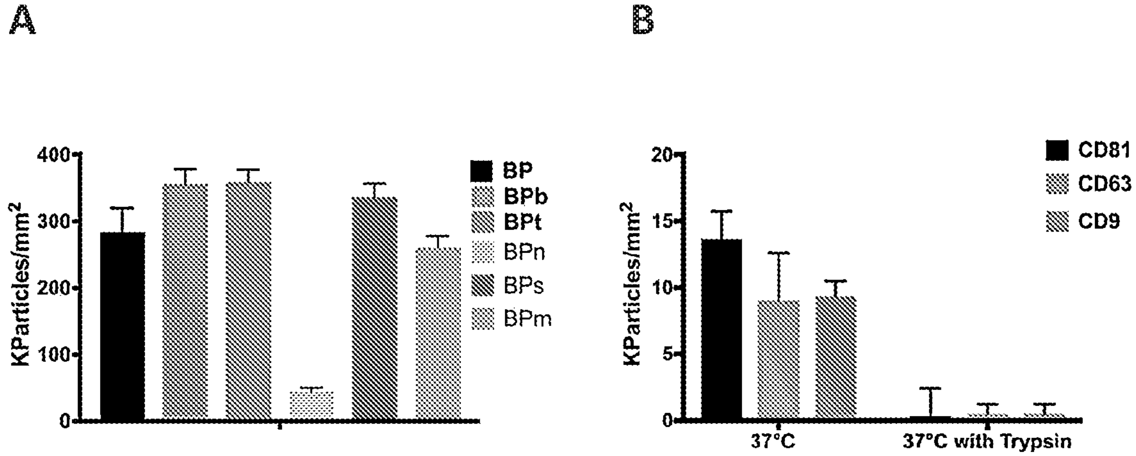
FIG. 21: (A): Particle density for SEC isolated EVs form human serum incubated at the concentration of $1\times10^9$ particles/mL. EVs capturing by BP peptides is not affected by trypsin treatment. (B) EVs binding on CD81/CD63/CD9 antibody chip is abolished by surface protein digestion using trypsin.

In order to get insights into the EV-peptide binding mechanism and verify if it is only mediated by the lipid membrane and not by its associated proteins, serum EVs isolated by SEC were subjected to trypsin digestion, quantified by NTA (FIG. 20) and incubated at the concentration of $1\times10^9$ particles/mL on peptide microarrays (FIG. 21A).

Trypsin Treatment

To hydrolyze membrane proteins, SEC sample was incubated with 25 μg/mL Trypsin for 6 hours at 37° C. in a Eppendorf Thermomixer according to [26, 27]

Particle density on BP spotted peptides, for the trypsin-treated sample compared to that of a sample subjected to analogous incubation in absence of proteolytic enzyme, demonstrated that membrane protein digestion doesn't affect vesicles binding. Indeed, binding in some cases (namely with the multivalent peptides) is even enhanced by proteolysis and thus not mediated by surface associated proteins. Oppositely, when the same samples were incubated on an antibody (CD81/CD63/CD9) Tetraspanin Kits provided by NanoView Biosciences (Boston MA) chip, as expected, no binding was detectable on the trypsin digested sample (FIG. 21B).

Example 2: Capturing and Analysis by Fluorescence Microarrays of EVs Isolated from Human Serum by UC and SEC and from Pure Human Serum BP peptides were spotted on silicon slides coated by copoly Azide (see example 1).

The slides are spotted using a non-contact spotter sciFLEXARRAYER S12. Each slide is spotted in order to obtain sixteen identical subarrays. After the spotting, the slides are placed in a humid chamber at room temperature overnight. Subsequently, the slides are incubated for 60 minutes in a solution of 2 mM EDTA. After that, the silicon supports are washed in deionized water and dried with a nitrogen stream.

The slides are subjected to dynamic incubation with samples for 60 minutes at room temperature and then overnight at 4° C.

Purified samples are generally used with no dilution (concentration of $10^{11}$ particles/ml) or they can be diluted 25:1 (25 μl of serum and 1 μl of 20× concentrated incubation buffer) with Incubation Buffer (0.5 M Tris/HCl—pH 7.6, 1.5 M NaCl, 0.2% Tween 20).

After sample incubation slides undergo a dynamic washing with Washing Buffer (0.05 M Tris/HCl pH 9, 0.25 M NaCl, 0.05% v/v Tween 20), then with PBS for 2 minutes and dried.

Then, the slides are incubated with a mixture of biotinylated antibodies of detection (Ab CD9, Ab CD63, Ab CD81 from Adipogen Lifescience) 1 mg/ml diluted 1:1500 in Incubation Buffer (0.5 M Tris/HCl—pH 7.6, 1.5 M NaCl, 0.2% Tween 20). The dynamic incubation with detection antibodies takes 2 hours at room temperature.

The silicon supports undergo a further dynamic washing with Washing Buffer for 10 minutes and then are briefly washed with PBS and dried with current of nitrogen.

The slides are then incubated with Cy3-Streptavidin or Cy5 (Alexa Fluor 647)-conjugated Streptavidin 1 mg/ml diluted 1:1500 in Incubation Buffer (0.5 M Tris/HCl—pH 7.6, 1.5 M NaCl, 0.2% Tween 20) for 30 minutes in dynamic mode and in dark.

In the end, the supports are washed in dynamic mode with PBS for 10 minutes, with deionized water and dried with current of nitrogen.

Fluorescence is detected by a fluorescence scanner, generally it is used a 100% laser power and 200% Gain. The results are provided as intensity of fluorescence of each spot expressed as data normalized by subtraction of the background.

Figure 22:
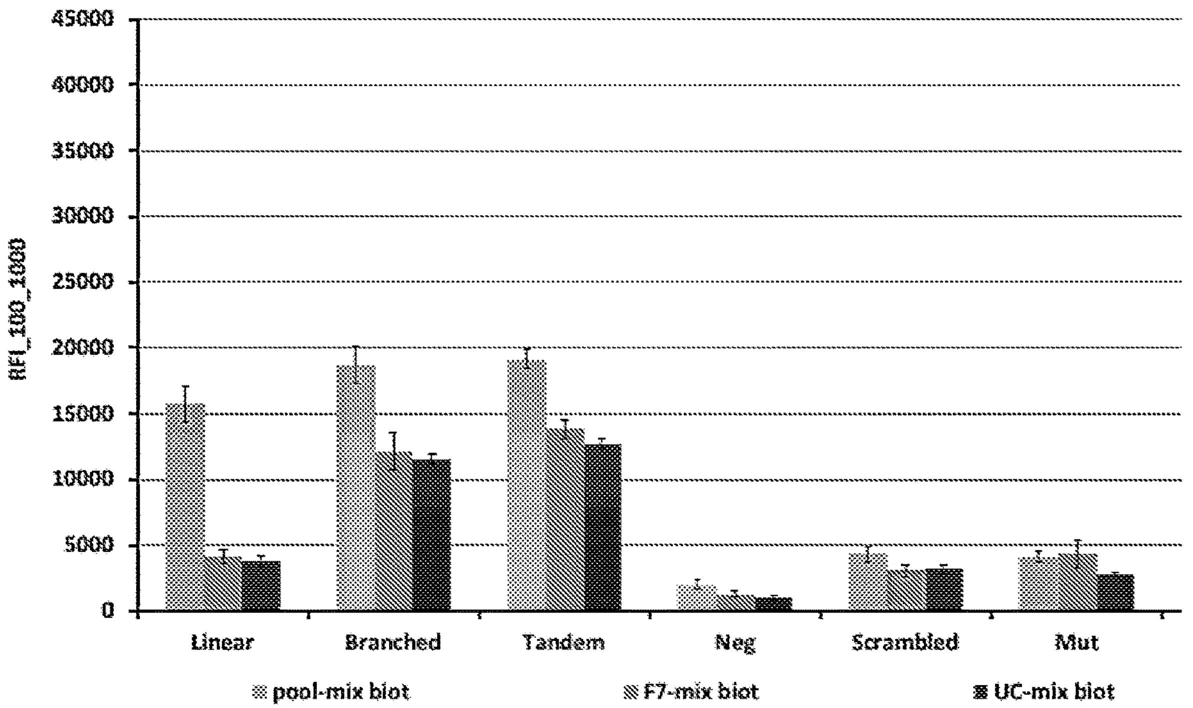
FIG. 22: fluorescence intensity after incubation with anti-CD9/CD63/CD81 antibodies of EVs from SEC isolation, UC isolation and a pure pool of sera by BP peptides spotted on silicon slides.

FIG. 22 shows fluorescence intensity of EVs detected at 100% of Laser power and photomultiplier gain.

BP peptides capture EVs from all the three tested samples, fluorescence signal on BPn is negligible, multivalency enhance EV capturing capacity.

Example 3: Capturing and Analysis of EVs Isolated from Human Serum and SEC and from Pure Human Serum by BP-Modified Hydrogels Recently, a soft peptide hydrogel for applications in the microanalytic field was developed using a self-assembling peptide hydrogelator [28]. This strategy yielded a stable and yet highly permeable matrix that enables for controlled size-dependent biomolecules diffusion based on peptide monomer concentration. Remarkably, the supramolecular hydrogel forms rapidly (<1 h) and spontaneously from a single peptide monomer and it is compatible with microarray fabrication due to favourable viscoelastic properties. Additionally, the material exhibits self-adhesive properties on hydrophobic polymethyl metacrylate (PMMA) surfaces and silicon slides, that we exploited for its direct integration on microarray chips. To develop this highly versatile material, we used a 13 residues amino acid stretch (Ac-YFQQKFQFQFEQQ-conh2, YF-Q11) that forms soft hydrogels in a wide micromolar concentration range (25-500 uM).

Gel permeation to biomolecules was assessed under typical operative steps of microarray immunoassay protocols, using fluorescent labelled biomolecules. The fast diffusion of differently sized biomolecules was strictly bound to YF-Q11 concentration, which can be tuned to control differential analytes permeability through the matrix. At 25 uM YF-Q11 concentration, free and complete diffusion occurs in approximately 2 minutes for all tested biomolecules.

Given these premises, the possibility was demonstrated to entrap EVs within the YF-Q11 hydrogel modified by BP peptides through a co-assembly strategy and to probe them with EVs-selective affinity probes (anti-tetraspanins antibodies and peptide affinity probes).

Freshly lyophilized YF-Q11 aliquots were dissolved in milliQ water to 500 uM concentration. Resulting solution was then sonicated for 5 min, diluted to desired concentration and then incubated at 40° C. for 2 hours. The resulting soft hydrogels were functionalized with BP by a co-assembling strategies with BP conjugated to YF-Q11 and used for isolation and analysis on microarrays of EVs.

Covalent conjugates of BP peptides with YF-Q11 were obtained via a click chemistry approach, and added at a 10% ratio in the YF-Q11 hydrogel matrix during the pre-printing step at 40° C. The BP-conjugate self-assemble within the YF-Q11 hydrogel.

BP-functionalized hydrogels were mixed with purified exosomes extracted from human serum to obtain a vesicles suspension of $5*10^9$ particles/mL and spotted with sciFLEXARRAYER S12 on silicon slides. Empty BP-hydrogels were spotted on slides as negative controls.

Figure 23:
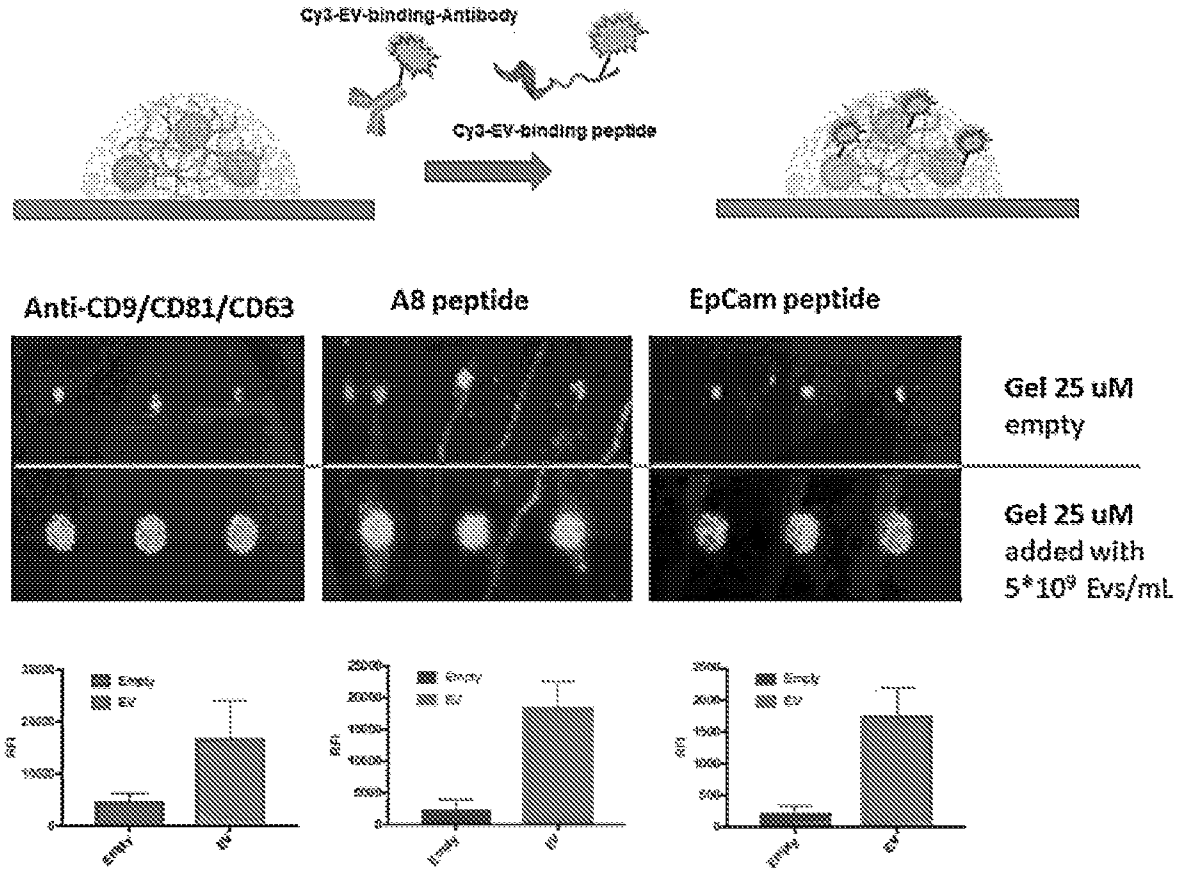
FIG. 23: top panel: scheme of the method. Hydrogels functionalized by BP peptides entrap EVs being permeable to contaminants and to fluorescent probes. Fluorescent signals are detectable after incubation with antitetraspanins antibodies and fluorescent peptide aptamers. Fluorescence in empty gels is negligible.

Slides were washed 5 minutes in PBS to allow contaminants to permeate out of the hydrogel spots and then and the microarray was incubated with a mixture of antibodies directed against the tetraspanins CD9, CD81, CD63 or with fluorescently labelled peptides A8 or EPCAM-p. Tetraspanins are known exosomes markers, A8 and EPCAM-p are peptide aptamers that, according to the literature, have affinity for EVs membrane proteins HSP70 a Epithelial Cell surface Antigen, respectively. A clear fluorescence response is detectable on EVs containing hydrogel spots demonstrating vesicles entrapment and permeation to fluorescent affinity probes (FIG. 23). Negligible signals were instead detected in empty control spots.

Figure 24:
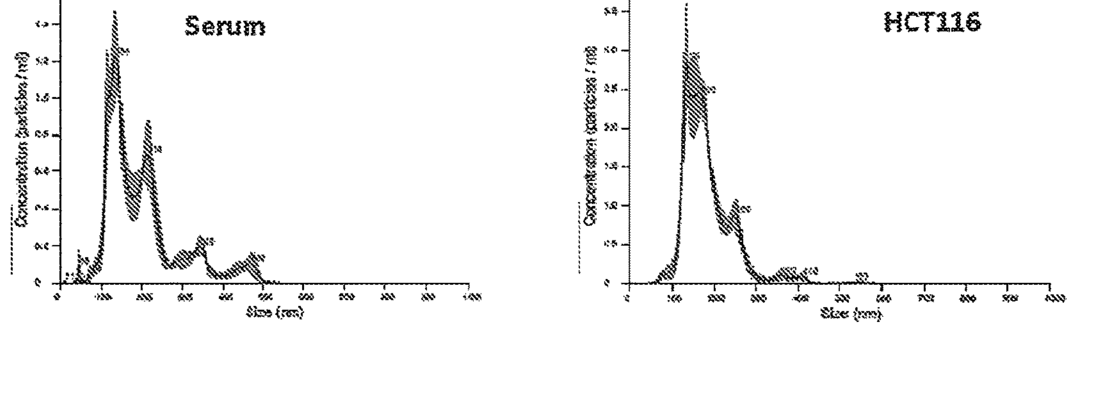
FIG. 24: a pool of human serum and EVs from HCT cell lines were characterized by NTA (upper panel) and entrapped in the BP modified hydrogel. Fluorescent signals are detectable after incubation with antitetraspanins antibodies and fluorescent peptide aptamers. Fluorescence in empty gels is negligible.
Figure 24:
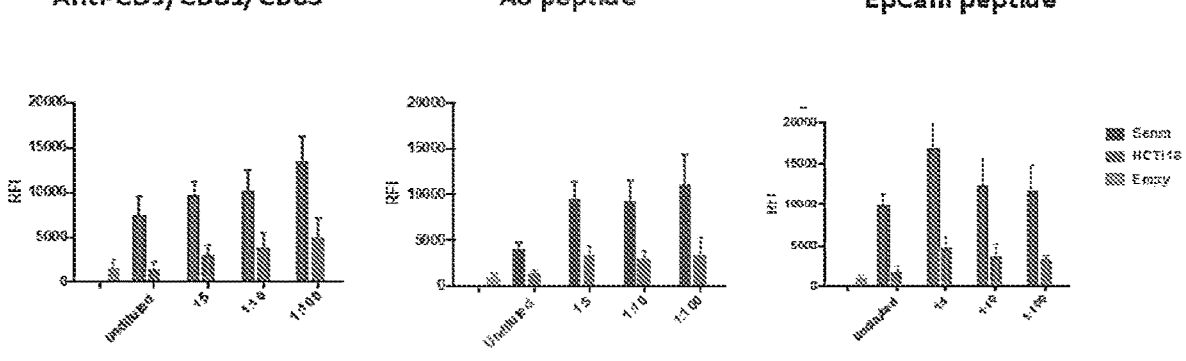

The same experiment was repeated adding to 25 uM BP-functionalized YF-Q11 gel two different complex samples: an healthy serum and a HCT116 (human colorectal cancer cell line) culture medium pre-cleared from cell debris. The two samples contain $1.2*10^{11}$ and $2.6*10^9$ particles/mL respectively (FIG. 24), as characterized by NTA (Nanoparticle Tracking Analysis). Undiluted or diluted samples were added in a fixed 1:30 v/v ratio to the hydrogel, spotted, washed for 5 minutes to allow contaminants to out-diffuse, and incubated with antibodies directed against the tetraspanins CD9, CD81, CD63 or with fluorescently labelled peptides A8 or EPCAM-p. Again, results clearly highlighted a significant difference between sample-containing and empty controls, strengthening the previous data obtained with purified EVs (FIG. 24).

CITED REFERENCES

[1] van Niel, G. et al.: Shedding light on the cell biology of extracellular vesicles. Nature Reviews Molecular Cell Biology, 19, 213-228 (2018). http://doi:10.1038/nrm.2017.125.

[2] E L Andaloussi, S. et al.: Extracellular vesicles: biology and emerging therapeutic opportunities. Nature reviews. Drug discovery, 12, 347-57 (2013). http://doi:10.1038/nrd3978.

[3] Konoshenko, M. Y. et al.: Isolation of Extracellular Vesicles: General Methodologies and Latest Trends. BioMed Research International, 2018, 1-27 (2018). http://doi:10.1155/2018/8545347.

[4] Merchant, M. L. et al.: Isolation and characterization of urinary extracellular vesicles: Implications for biomarker discovery. *Nat. Rev. Nephrol*. (2017), 13, 731-749

[5] Jørgensen, M. et al.: Extracellular Vesicle (EV) Array: microarray capturing of exosomes and other extracellular vesicles for multiplexed phenotyping. Journal of extracellular vesicles, 2, 1-9 (2013). http://doi:10.3402/jev.v2i0.20920.

[6] Rojalin, T. et al.: Nanoplasmonic Approaches for Sensitive Detection and Molecular Characterization of Extracellular Vesicles. Frontiers in Chemistry, 7 (2019). http://doi:10.3389/fchem.2019.00279.

[7] Daaboul, G. G. et al.; Ünlü, M. S.; Chiari, M.: Digital Detection of Exosomes by Interferometric Imaging. Scientific Reports, 6 (2016). http://doi:10.1038/srep37246.

[8] van Niel, G. et al.: Shedding light on the cell biology of extracellular vesicles. Nature reviews. Molecular cell biology, (2018). http://doi:10.1038/nrm.2017.125.

[9] György, B. et al.: Membrane vesicles, current state-of-the-art: Emerging role of extracellular vesicles. *Cell. Mol. Life Sci*. (2011), 68, 2667-2688

[10] Hugel, B. et al.: Membrane Microparticles: Two Sides of the Coin. Physiology, 20, 22-27 (2005). http://doi:10.1152/physiol.00029.2004.

[11] Kastelowitz, N. et al.: Exosomes and microvesicles: Identification and targeting by particle size and lipid chemical probes. *ChemBioChem* (2014), 15, 923-928

[12] Lemmon, M. A.: Membrane recognition by phospholipid-binding domains. *Nat. Rev. Mol. Cell Biol*. (2008)

[13] Antonny, B.: Mechanisms of Membrane Curvature Sensing. Annual Review of Biochemistry, (2011). http://doi:10.1146/annurev-biochem-052809-155121.

[14] Cui, H. et al.: Mechanism of membrane curvature sensing by amphipathic helix containing proteins. Biophysical Journal, (2011). http://doi:10.1016/j.bpj.2011.01.036.

[15] Hatzakis, N. S. et al.: How curved membranes recruit amphipathic helices and protein anchoring motifs. Nature Chemical Biology, (2009). http://doi:10.1038/nchembio.213.

[16] Bhatia, V. K. et al.: Amphipathic motifs in BAR domains are essential for membrane curvature sensing. EMBO Journal, (2009). http://doi:10.1038/emboj.2009.261.

[17] Bigay, J. et al.: ArfGAP1 responds to membrane curvature through the folding of a lipid packing sensor motif. EMBO Journal, (2005). http://doi:10.1038/sj.emboj.7600714.

[18] De Jesus, A. J. et al.: Determinants of Curvature-Sensing Behavior for MARCKS-Fragment Peptides. Biophysical Journal, 110, 1980-1992 (2016). http://doi:10.1016/j.bpj.2016.04.007.

[19] Flynn, A. D. et al.: Lipid-Targeting Peptide Probes for Extracellular Vesicles. Journal of Cellular Physiology, 231, 2327-2332 (2016). http://doi:10.1002/jcp.25354.

[20] Gómez-Llobregat, J. et al.: Anisotropic Membrane Curvature Sensing by Amphipathic Peptides. Biophysical Journal, 110, 197-204 (2016). http://doi:10.1016/j.bpj.2015.11.3512.

[21] De Jesus, A. J. et al.: Computational design of membrane curvature-sensing peptides. In *Methods in Molecular Biology*; (2017); Vol. 1529, pp. 417-437

[22] Saludes, J. P. et al.: Multivalency amplifies the selection and affinity of bradykinin-derived peptides for lipid nanovesicles. Molecular BioSystems, (2013). http://doi:10.1039/c3mb70109c.

[23] Gori, A. et al.: Multiple epitope presentation and surface density control enabled by chemoselective immobilization lead to enhanced performance in IgE-binding fingerprinting on peptide microarrays. Analytica Chimica Acta, (2017). http://doi:10.1016/j.aca.2017.06.027.

[24] Gori, A. et al.: Screening Complex Biological Samples with Peptide Microarrays: The Favorable Impact of Probe Orientation via Chemoselective Immobilization Strategies on Clickable Polymeric Coatings. Bioconjugate Chemistry, 27, 2669-2677 (2016). http://doi:10.1021/acs.bioconjchem.6b00426.

[25] Théry, C. et al.: Minimal information for studies of extracellular vesicles 2018 (MISEV2018): a position statement of the International Society for Extracellular Vesicles and update of the MISEV2014 guidelines. Journal of Extracellular Vesicles, 7, 1535750 (2018). http://doi:10.1080/20013078.2018.1535750.

[26] Cvjetkovic, A. et al.: 2016. Detailed Analysis of Protein Topology of Extracellular Vesicles-Evidence of Unconventional Membrane Protein Orientation. Sci. Rep. doi:10.1038/srep36338

[27] Skliar, M. et al.: 2018. Membrane proteins significantly restrict exosome mobility. Biochem. Biophys. Res. Commun. 501, 1055-1059. doi:10.1016/j.bbrc.2018.05.107

[28] Gagni, P. et al.: 2019. A self-assembling peptide hydrogel for ultrarapid 3D bioassays. Nanoscale Adv. 1, 490-497. doi:10.1039/C8NA00158H

What is claimed is:

1. A molecular probe comprising at least one first moiety and at least one second moiety which are each covalently bound to the molecular probe, wherein:

the at least one first moiety comprises at least one binding peptide or peptidomimetic for binding the molecular probe to at least one extracellular vesicle (EV) membrane, wherein the binding is mediated by EV membrane curvature sensing and wherein the peptide or peptidomimetic is derived from a curvature sensing peptide or protein domain; and the at least one second moiety comprises at least one support binding group for binding of the molecular probe to at least one support, the support binding group is bound to the at least one support and reacts with an azide, alkyne, thiol, alkene, amine, aldehyde, maleimide or polyhistidine binding group on the support, and the peptide or peptidomimetic is derived from Bradykinin.

2. The probe of claim 1, wherein the peptide or peptidomimetic is bound to the at least one extracellular vesicle membrane.

3. The probe of claim 1, wherein the support is a solid support or a semi-solid support selected from the group consisting of a chip, a slide, a bead, a well, a hydrogel, a resin, a polymer, a filter, a membrane, a microarray, a hydrogel and a peptide hydrogel.

4. The probe of claim 1, wherein the extracellular vesicle is an exosome, a microvesicle, a synthetic lipidic nanovesicle or a synthetic lipidic microvesicle.

5. The probe of claim 1, wherein the first moiety comprises the peptide, and the peptide is a cationic peptide.

6. The probe of claim 1, wherein the peptide or peptidomimetic is linear, branched, cyclic, tandem, multimeric, multidomain, or multivalent.

7. The probe of claim 1, wherein the peptide or peptidomimetic is dimeric.

8. The probe of claim 1, wherein the support binding group comprises azide, alkyne, thiol, alkene, amine, carboxylic acid, aldehyde, or maleimide.

9. The probe of claim 1, wherein the support binding group comprises propargyl.

10. The probe of claim 1, wherein the probe further comprises at least one third moiety which is covalently bound to the molecular probe and which is a spacer between the first moiety and the second moiety.

11. The probe of claim 10, wherein the spacer is a single amino acid, an amino acid sequence, an organic moiety, or a cleavable spacer.

12. The probe of claim 10, wherein the spacer comprises poly(ethylene glycol), lysine, or glycine.

13. The probe of claim 1, wherein the probe further comprises at least one fourth moiety which is a label, wherein the label is a fluorescent label.

14. A molecular probe comprising at least one first moiety and at least one second moiety which are each covalently bound to the molecular probe, wherein:

the at least one first moiety comprises at least one binding peptide or peptidomimetic for binding the molecular probe to at least one extracellular vesicle (EV) membrane, wherein the binding is mediated by EV membrane curvature sensing and wherein the peptide or peptidomimetic is derived from a curvature sensing peptide or protein domain; and the at least one second moiety comprises at least one support binding group for binding of the molecular probe to at least one support, the support binding group is bound to the at least one support and reacts with an azide, alkyne, thiol, alkene, amine, aldehyde, maleimide or polyhistidine binding group on the support, and the peptide or peptidomimetic is MARCKS, Synaptotagmin, Magainin, arfgap1, α-synuclein, Synapsin (I), Endophilin, c-reactive protein, or Amphiphysin.

* * * * *

SEQUENCE LISTING

```
<160> NUMBER OF SEQ ID NOS: 6

<210> SEQ ID NO 1
<211> LENGTH: 9
<212> TYPE: PRT
<213> ORGANISM: Unknown
```

```
<220> FEATURE:
<221> NAME/KEY: source
<223> OTHER INFORMATION: /note="Description of Unknown:
      Bradykinin peptide sequence"

<400> SEQUENCE: 1

Arg Pro Pro Gly Phe Ser Pro Phe Arg
1               5


<210> SEQ ID NO 2
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Tyr Phe Gln Gln Lys Phe Gln Phe Gln Phe Glu Gln Gln
1               5                   10


<210> SEQ ID NO 3
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 3

Arg Pro Pro Gly Phe Ser Pro Phe Arg Lys Gly
1               5                   10


<210> SEQ ID NO 4
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 4

Glu Pro Pro Gly Phe Ser Pro Phe Glu Glu Gly
1               5                   10


<210> SEQ ID NO 5
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 5

Gly Arg Pro Pro Arg Pro Ser Phe Phe Lys Gly
1               5                   10


<210> SEQ ID NO 6
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic probe"
```

-continued

```
<400> SEQUENCE: 6

Arg Pro Ala Gly Phe Ser Ala Phe Arg Lys Gly
1               5                   10
```